United States Patent [19]
Kondo et al.

[11] Patent Number: 5,480,535
[45] Date of Patent: Jan. 2, 1996

[54] THIN FILM MULTILAYERED AIR/FUEL RATIO SENSOR

[75] Inventors: Haruyoshi Kondo, Anjo; Hideaki Takahashi; Keiichi Saji, both of Aichi; Masaharu Takeuchi, Owariasahi; Kozo Satta, Nagoya, all of Japan

[73] Assignee: Kabushiki Kaisha Toyota Chuo Kenkyusho, Aichi, Japan

[21] Appl. No.: 174,126

[22] Filed: Dec. 27, 1993

[30] Foreign Application Priority Data

Dec. 28, 1992 [JP] Japan .................................. 4-361142
Aug. 12, 1993 [JP] Japan .................................. 5-220630

[51] Int. Cl.$^6$ .......................... G01N 27/41; G01N 27/409
[52] U.S. Cl. .......................... 204/425; 204/424; 204/426
[58] Field of Search .......................... 204/421–429

[56] References Cited

U.S. PATENT DOCUMENTS

| | | | |
|---|---|---|---|
| 4,416,763 | 11/1983 | Fujishiro | 204/426 |
| 4,487,680 | 12/1984 | Logothetis et al. | 204/426 |
| 4,574,627 | 3/1986 | Sakurai et al. | 204/426 |
| 4,712,419 | 12/1987 | Ikai et al. | 204/425 |
| 4,844,788 | 7/1989 | Takahashi et al. | 204/412 |
| 4,851,105 | 7/1989 | Ishiguro et al. | 204/429 |
| 5,049,254 | 9/1991 | Logothetis et al. | 204/426 |

FOREIGN PATENT DOCUMENTS 59-108951  6/1984  Japan .

*Primary Examiner*—T. Tung
*Attorney, Agent, or Firm*—Oblon, Spivak, McClelland, Maier & Neustadt

[57] ABSTRACT

A thin film mutilayered air-fuel ratio sensor having a sensor element including a first electrode formed on a porous substrate, a first solid electrolyte and a third electrode formed on the first electrode in this order, in such a manner that the first electrode is completely covered by the first solid electrolyte inclusive of its surroundings, and that the first solid electrolyte is completely covered by the third electrode inclusive of its surroundings, a second solid electrolyte and a fourth electrode and formed on the third electrode in this order, in such a manner that the peripheral portion of the third electrode is left uncovered by the second solid electrolyte and the fourth electrode and thereby left exposed. The first electrode, the third electrode, and the fourth electrode are made of a gas-permeable porous platinum, and the first solid electrolyte and the second solid electrolyte are made of a gas-permeable dense solid electrolyte having oxygen ion conductivity. The sensor has far improved performance as compared to the conventional ones and can be made compact.

11 Claims, 22 Drawing Sheets

CURRENT-VOLTAGE (I-V) CHARACTERISTICS

CURRENT-AIR EXCESS RATE CHARACTERISTICS

CURRENT-VOLTAGE (I-V) CHARACTERISTICS

CURRENT - AIR EXCESS RATE CHARACTERISTICS

THIN FILM MULTILAYERED AIR/FUEL RATIO SENSOR

BACKGROUND OF THE INVENTION

1. Field of the Invention

The present invention relates to a thin film multilayered air-fuel ratio sensor. More particularly, the present invention relates to a compact high-performance thin film multilayered air-fuel ratio sensor.

2. Description of the Related Art

Various types of air-fuel ratio sensors have been used to present. Oxygen sensors belong to a type of such sensors. This type of sensor is widely used, for example, as an air-fuel ratio sensor for controlling engines of automobiles. The oxygen sensors falling in the category of the air-fuel ratio sensors can be further classified chiefly into three types; i.e., a resistance type oxygen sensor which utilizes change in resistance of an oxide semiconductor, an oxygen concentration cell type oxygen sensor using a solid electrolyte, and an oxygen pump type oxygen sensor. The sensors belonging to the last type include not only those already put into practice but also those still under research or development. The characteristic features of those three types of sensors are each described in further detail below.

The resistance type oxygen sensors, which are based on the change of resistance of an oxide semiconductor, can be further classified into those making use of an n-type semiconductor such as $TiO_2$, $Nb_2O_5$, and $SnO_2$, and the ones using a p-type semiconductor such as $CoO$ and $CoO_{1-x}Mg_x$. The resistance type oxygen sensor detects the resistance of an oxide semiconductor which changes as a function of the oxygen partial pressure according to the following equation (I):

$$R = P_o^{1/n} \quad (I)$$

where, R represents the resistance of the oxide semiconductor; $P_o$ represents the oxygen partial pressure; and n represents a value of from +4 to +6 for a p-type semiconductor and from −4 to −6 for an n-type semiconductor.

When a motorcar is in motion at an air ratio λ of 1, the oxygen partial pressure changes drastically within a range of from $10^{-0.2}$ to $10^{-30}$ atm. Accordingly, the resistance of an oxide semiconductor also changes rapidly over 3 to 4 figures in accordance with the change in oxygen partial pressure at an air ratio λ=1. Based on this rapid change in characteristics, the resistance type oxygen sensor is used as a sensor for detecting the theoretical air-fuel ratio.

An oxygen concentration cell type oxygen sensor takes advantage of a solid electrolyte. This type of sensor is equipped with a sensor element, for example, a cylinder having one sealed end and made of a zirconia solid electrolyte. Thus, the difference between the oxygen partial pressure of the discharge side and that of the side exposed to atmosphere is detected as an electromotive force according to the following equation (II):

$$E = \frac{RT}{4F} \ln \frac{P_o'}{P_o} \quad (II)$$

where, R is the gas constant; T represents absolute temperature; F is the Faraday constant; $P_o'$ represents the oxygen partial pressure of the cathode side; and $P_o$ represents the oxygen partial pressure of the anode side.

It can be seen from the equation that, upon running an automobile at an air ratio λ of 1, an electromotive force in the range of from 0 to 1 V is generated in an oxygen concentration cell type oxygen sensor, corresponding to the rapid change in oxygen partial pressure. Accordingly, a point at which an electromotive force of 0.5 V is obtained is detected as the theoretical air-fuel ratio (at air ratio λ=1).

An oxygen pump type oxygen sensor makes use of an electrochemical pump to measure the conductivity of oxygen ions within an electrolyte. This type of sensors can be further classified into the following three types depending on the difference in basic constitution.

(A) A type using an oxygen pump cell for monitoring $O_2$;

(B) A type using an oxygen pump cell together with a leak hole; and (C) A type using an oxygen pump cell for monitoring $O_2$, which is used in combination with a leak hole.

Furthermore, there are also three types of known methods for detecting the oxygen concentration in an oxygen pump type oxygen sensor. In the first method, the time necessary for pumping oxygen is measured to know the oxygen concentration; in the second method, the limit current is measured to determine the oxygen concentration; and, in the third method, the voltage upon applying a constant current is detected to measure the oxygen concentration. It can be seen that an oxygen pump type oxygen sensor enables the detection of an oxygen concentration over a wide range. Accordingly, this type of oxygen sensor is used particularly as an air-fuel ratio sensor applicable over a wide band range.

Zirconia oxygen concentration cell type sensors and titania resistance type oxygen sensors have been widely used heretofore as the theoretical air-fuel ratio sensors. Both types of sensors respond with an output (electromotive force or resistance) which changes abruptly with a change in equilibrium oxygen partial pressure at the theoretical air-fuel ratio; i.e., they exhibit the so-called Z-characteristics. Accordingly, the use of those sensors enables one to easily judge whether the air-fuel ratio of interest falls in a lean region (referred to hereinafter simply as "lean region") or in a rich region by comparing the obtained output with a proper reference value (either a voltage or a resistance) selected for each of the theoretical air-fuel ratio sensors.

In a zirconia oxygen concentration cell type air-fuel ratio sensor, the difference in the electromotive force among sensors is small, and the electromotive force has small temperature dependence. Accordingly, the sensing portions can be readily replaced by another sensing portion of the same type. Moreover, when the sensor is mounted on an exhaust system of an automobile, the theoretical air-fuel ratio can be detected with high precision even when a reference potential is fixed constant and the exhaust system is subjected to temperature change. These are the advantageous features of the zirconia oxygen concentration cell type air-fuel ratio sensor. Thus, the sensors of this type are most convenient for controlling the air-fuel ratio of a motorcar engine equipped with a ternary catalyst, and are therefore most frequently used for the above purpose.

In a titania ($TiO_2$) resistance type oxygen sensor, the resistance of the entire $TiO_2$ resistor changes in accordance with the oxygen partial pressure of the atmosphere. Thus, a reference oxygen partial pressure need not be set upon measuring the oxygen concentration. Since a reference electrode and a gas inlet for the reference electrode are unnecessary, this type of oxygen sensor can be built into a compact and simple structure. Accordingly, the sensors of this type are gradually increasing in number in the application of controlling the air-fuel ratio of automobiles.

Considering the air-fuel ratio sensors applicable to a broad range of air-fuel ratio, limiting current type multi-range air-fuel ratio sensors using zirconia are dominant. Advantageously, the temperature dependence of the sensor electromotive force and the output current of the sensors of this type are both very low. Accordingly, they are extremely convenient and are thereby most frequently sed among the multi-range air-fuel ratio sensors.

The conventional sensors, e.g., a zirconia oxygen concentration cell type theoretical air-fuel ratio sensor and a zirconia limiting current type multi-range air-fuel ratio, posses excellent properties as enumerated above, however, they are still confronted with the following problems which are yet to be solved.

(1) Achievement of the measurement of a theoretical air-fuel ratio with a precision of about ±0.1% using a single air-fuel ratio sensor;

(2) Realization of the measurement of an air-fuel ratio with a precision of about ±1% over the entire range covering both the lean region and the rich region using a single air-fuel ratio sensor;

(3) Detection of the air-fuel ratio with high precision immediately after starting the engine;

(4) Reducing the power consumption of the sensor as much as possible to lower the fuel consumption of the automobile; and (5) Implementing a sensor of a simpler structure to reduce the production cost.

In recent years, more severe regulation against motor car exhaust are requested every year in the United States of America as well as in Europe and Japan. Accordingly, not only improvements in motor car engine performance and in purifying performance of the catalyst are required, but also a strict requirement on air-fuel ratio sensors is demanded. These requirements can not be coped with by a simple modification of the prior art technology.

More specifically, the present day requirements can be described as follows:

(A) A motorcar engine which consumes less fuel and discharges less harmful exhaust gas is required from the viewpoint of preventing global environmental destruction from occurring. At the same time, the engine must provide high output when necessary. This requires the engine to have its air-fuel ratio precisely controlled to the theoretical air-fuel ratio. More preferably, the air-fuel ratio of the engine is set at the optimal air-fuel ratio from a lean region to a rich region according to the state of driving. To control the air-fuel ratio following faithfully the optimal air-fuel ratio, however, it is necessary to precisely detect the air-fuel ratio using an air-fuel ratio sensor and to perform feed-back control of the air-fuel ratio based on the detected value. Accordingly, it is necessary to precisely detect the theoretical air-fuel ratio and/or the air-fuel ratio over the entire range covering the lean region and the rich region.

(B) In a conventional air-fuel ratio sensor, the amount of hydrocarbon (HC) discharged immediately after igniting the engine but before the sensor is turned on accounts for a large fraction of the hydrocarbon discharged on starting up an engine from a cold state. The amount of discharged hydrocarbon is intimately related with whether the fuel supply is appropriately increased or not upon starting up the engine. Thus, the supply rate of the fuel upon starting up the engine must be optimized to reduce the amount of discharged hydrocarbon. This can be achieved only by rapidly turning on the air-fuel ratio sensor with the ignition of the engine. Furthermore, the exhaust gas is treated with an exhaust gas purifying catalyst to remove toxic components therefrom. The purifying performance of the catalyst can be fully ameliorated by precisely detecting the theoretical air-fuel ratio. This requires a high precision air-fuel ratio sensor which accurately detects the theoretical air-fuel ratio and/or air-fuel ratio over a wide range.

However, the air-fuel ratio sensor, particularly, the sensing portion for detecting the air-fuel ratio, must be brought to a temperature suited for the operation, because the sensing portion of the air-fuel ratio sensor functions only at a limited temperature of about 700° C. Thus, this inevitably requires the sensor to be rapidly heated to the desired temperature. In general, however, the rapid elevation of temperature causes the sensing portions to undergo breakage and degradation due to thermal strain. It is therefore necessary to make the air-fuel ratio sensor compact to suppress thermal stress and thereby lower such unfavorable effects.

In the case of a zirconia limiting current type air-fuel ratio sensor, it is required that the theoretical air-fuel ratio be detected at high precision and that the entire range covering the leaning region and the rich region be measured by the same single sensor. These demands can be accomplished by maintaining both the anode and cathode air-tight, and also separated from each other. The electrode on the side not exposed to the exhaust gas must be supplied with oxygen (air) at a high concentration. Thus, a path for introducing air (atmosphere) must be established from the outside of the sensor to the air-fuel ratio detector portion. Accordingly, in general, a cylindrical sensor element having a sealed end, i,e., a sensor element shaped like a drink glass, is used. However, the element of this type has limitations in reducing the size.

(C) If more electric power should be consumed for heating the air-fuel ratio sensor, it inevitably requires scaling up of equipments such as generators and batteries to meet the demand for power supply. This leads to an increase in the overall power consumption. To reduce the overall power consumption, it is necessary to reduce the power consumption of the air-fuel ratio sensor, however, it is also requisite and effective to make the sensor more functional.

As described in the foregoing, a conventional zirconia oxygen concentration cell type theoretical air-fuel ratio sensor requires a standard electrode to detect the theoretical air-fuel ratio. This inevitably involves additional installations of a mechanism for introducing air into the sensor and a mechanism for generating oxygen. However, a theoretical air-fuel ratio sensor of this type which requires externally introducing air into the sensor should be equipped with a voluminous air path having a complicated structure. It is extremely difficult to produce such a voluminous and complicate sensor. Furthermore, heat radiation loss also increases with increasing size of the sensor to further increase the power consumption. Moreover, the sensor becomes more apt to suffer thermal distortion as it becomes larger in size. Accordingly, a large sensor is unfeasible for rapid heating. This signifies that a longer starting up time is to be taken if a large theoretical air-fuel ratio sensor should be used. Thus, it can be seen that the aforementioned theoretical air-fuel ratio sensor on a motorcar not only consumes additional electric power to thereby unfavorably influence the total power consumption of the motorcar, but also has no contribution in reducing discharge of hydrocarbon upon cold starting up of the motorcar, because the sensor itself requires a longer start up time.

A prior art zirconia oxygen concentration cell type theoretical air-fuel ratio sensor having internally a mechanism for generating oxygen also requires a voluminous and complicate structure due to the built-in oxygen generation mechanism. It can be seen that the same problem discussed for the above theoretical air-fuel ratio sensor equipped with a mechanism for introducing air also applies to the sensor of the present type.

A prior art zirconia limiting current type oxygen sensor also requires the installation of a reference electrode having a mechanism for introducing air or for generating oxygen to detect the air-fuel ratio over the entire range. A sensor having no such means is applicable only to the lean region. Upon measuring the current for a rich region, however, it cannot be determined from the measured value alone whether it belongs to a lean region or a rich region, because the current in the rich region behaves as a two-valued function. This is the reason why an effective air-fuel ratio cannot be measured in the rich-region.

To overcome the difficulty above, it can be seen that an additional means for judging whether the measured value falls on a lean region or a rich region, another means for detecting the air-fuel ratio for the rich region, and also an additional means of oxygen pump composed of an electrochemical cell for supplying oxygen gas should be installed separately from the air-fuel ratio sensor for the lean region.

An multi-range air-fuel ratio sensor of a type which comprises externally introducing air into the sensor is basically characterized by its ability of detecting the air-fuel ratio over the entire range with high precision. However, the multi-range air-fuel ratio sensor of this type involves a large path having a complicate structure for introducing air, and the same problems as those discussed above in the case of zirconia oxygen concentration cell type theoretical air-fuel ratio sensor are left to be overcome.

SUMMARY OF THE INVENTION

The present invention has been accomplished with an aim to overcome the above problems for the prior art theoretical air-fuel ratio sensors.

An object of the present invention is to provide a compact and high performance oxygen concentration cell type theoretical air-fuel ratio sensor having a multilayered thin film structure (e.g., a zirconia oxygen concentration cell type theoretical air-fuel ratio sensor), which inherits the merits of a prior art oxygen concentration cell type theoretical air-fuel ratio sensor (e.g., a zirconia oxygen concentration cell type theoretical air-fuel ratio sensor) such as the ability of yielding an almost constant electromotive force even under change of temperature, but freed from an additional path for introducing air.

Another object of the present invention is to provide a compact and high performance limiting current type multi-range air-fuel ratio sensor having a multilayered thin film structure (e.g., a zirconia limiting current type multi-range air-fuel ratio sensor) and which enables detection of an air-fuel ratio over the entire range ranging from a lean to a rich region, which inherits the merits of a prior art limiting current type multi-range air-fuel ratio sensor (e.g., a zirconia limiting current type multi-range air-fuel ratio sensor) such as the ability of maintaining a low limiting current even under change in temperature, and yet having no additional path for introducing air.

Still another object of the present invention is to provide an air-fuel ratio sensor having a multilayered thin film structure and capable of detecting an air-fuel ratio over the entire range ranging from a lean region to a rich region, having excellent heat resistance and stability, yet capable of yielding an output less dependent on temperature change, and which can be considerably reduced in size by principle, said sensor comprising:

a combination of said oxygen concentration cell type theoretical air-fuel ratio sensor and said limiting current type multi-range air-fuel ratio sensor;

an integrated sensing portion for detecting the theoretical air-fuel ratio; and no path for introducing air.

A thin film multilayered air-fuel ratio sensor having a sensor element according to the first aspect of the present invention comprises:

a first electrode formed on a porous substrate;

a first solid electrolyte and a third electrode formed on the first electrode in this order, in such a manner that the first electrode completely covered by the first solid electrolyte inclusive of its surroundings, and that the first solid electrolyte is completely covered by the third electrode inclusive of its surroundings; and a second solid electrolyte and a fourth electrode formed on the third electrode in this order, in such a manner that the peripheral portion of the third electrode is left uncovered by the second solid electrolyte and the fourth electrode and thereby left exposed;

the first electrode, the third electrode, and the fourth electrode being made of a gas-permeable porous platinum, and the first solid electrolyte and the second solid electrolyte being made of a gas-impermeable dense solid electrolyte having oxygen ion conductivity.

A thin film multilayered air-fuel ratio sensor having a sensor element according to the second aspect of the present invention comprises:

a first electrode formed on a porous substrate;

a first solid electrolyte and a third electrode formed on the first electrode in this order, in such a manner that the first electrode is completely covered by the first solid electrolyte inclusive of its surroundings, and that the first solid electrolyte is completely covered by the third electrode inclusive of its surroundings;

a second solid electrolyte having an opening formed on the third electrode, in such a manner that a space is provided between the first solid electrolyte and the second solid electrolyte; and a fourth electrode formed on the side of the second solid electrolyte facing the third electrode and a fifth electrode formed on the side of the second solid electrolyte opposite to that facing the third electrode, the second electrolyte and the fifth electrode being formed in such a manner that the peripheral portion of the third electrode is left uncovered by them and thereby left exposed;

the first electrode, the third electrode, the fourth electrode, and the fifth electrode being made of a gas-permeable porous platinum, and the first solid electrolyte and the second solid electrolyte being made of a gas-impermeable dense solid electrolyte having oxygen ion conductivity.

In the first and second thin film multilayered air-fuel sensors, the second electrode may be provided with in addition to the first electrode, or the second electrode in place of the first electrode may be provided.

The thin film multilayered air-fuel ratio sensors according to the present invention have the aforementioned constitution, and thereby provides the following various effects.

(1) The sensor according to the present invention supplies oxygen to the sensor element by an oxygen pumping function. Thus, it is unnecessary to provide an air-introducing portion between the sensor element and the exterior of the housing, because the sensor element need not have an oxygen inlet portion. This enables a compact sensor.

(2) The sensor according to the present invention can be built into a planar structure. An oxygen inlet portion can be eliminated from the sensor element, and thereby the sensor element need not be built into a three-dimensional structure such as a cylinder as in the conventional type. The sensor according to the present invention can be produced favorably by film deposition technology.

(3) An air-tight structure can be easily achieved in the sensor according to the present invention, because the oxygen inlet portion can be omitted.

(4) The sensor according to the present invention is convenient for the practical measurement because it has small temperature dependence. This is achieved by integrating a portion for dissociating oxygen, a portion which functions as an oxygen pump, and a portion functioning as an oxygen concentration cell type theoretical air-fuel ratio sensor and/or a limiting current type multi-range air-fuel ratio sensor.

(5) In the oxygen concentration cell type theoretical air-fuel ratio sensor portion of the sensor according to the present invention, the theoretical air-fuel ratio can be measured accurately without involving any complicated operation such as adjusting the reference voltage depending on the temperature.

(6) In the limiting current type multi-range air-fuel ratio sensor portion of the sensor according to the present invention, an air-fuel ratio can be detected over the entire range ranging from a lean to a rich region without switching the applied voltage.

(7) The present invention provides a compact sensor which consumes low power.

(8) Since the sensor according to the present invention is produced by thin film deposition technology, it suffers very little thermal distortion even under rapid heating. Accordingly, a sensor with high stability is realized.

(9) Since the sensor according to the present invention is produced by thin film deposition technology, it can be readily put to mass production and thereby produced at a reduced cost.

(10) The sensor according to the present invention can be easily deformed and thereby used in various applications.

DETAILED DESCRIPTION OF THE INVENTION

Figure 1:
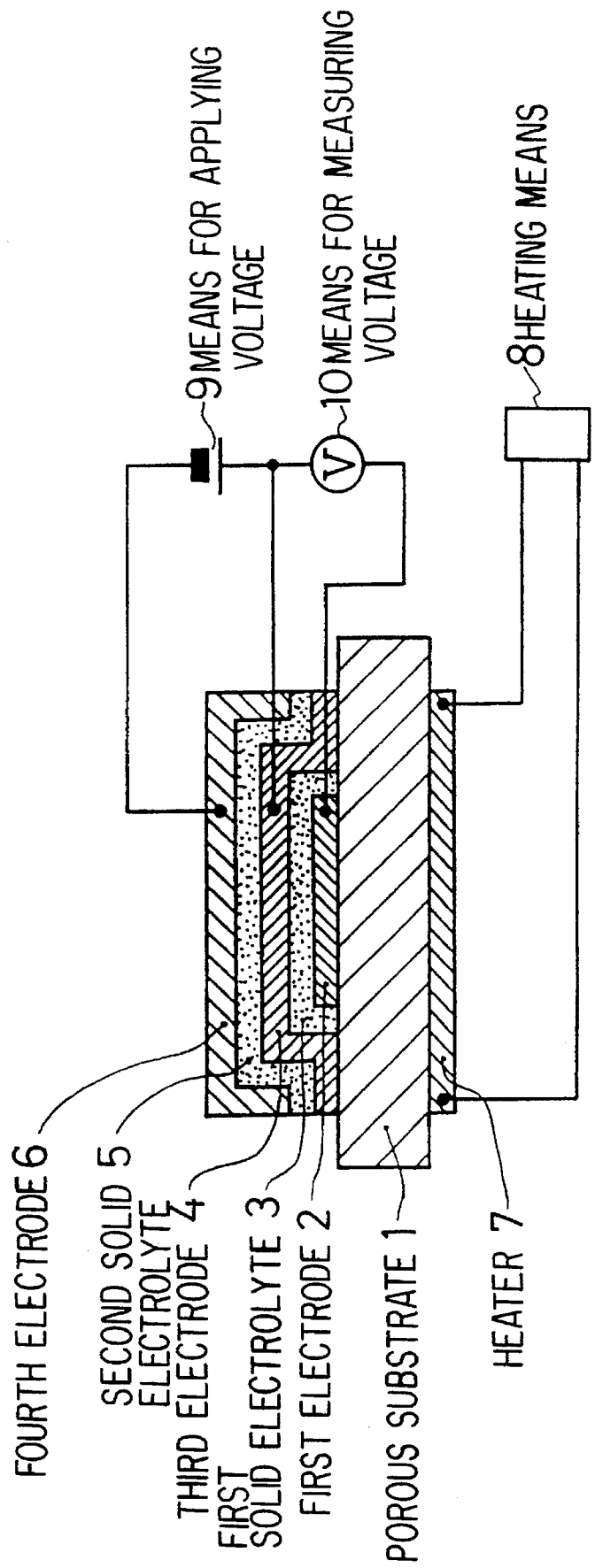
FIG. 1 is a schematic view illustrating an air-fuel ratio sensor according to EXAMPLE 1 of the present invention.

Referring to an air-fuel ratio sensor according to the first aspect of the invention, a plurality of fine grooves communicating with each other are preferably provided densely on the portion of the first electrode in contact with the porous substrate. In this manner, oxygen gas can be uniformly diffused over the entire surface of the first electrode. The size, shape, number, etc., of the grooves can be properly selected depending on conditions.

An air-fuel ratio sensor according to the first embodiment of the present invention preferably comprises a third electrode having densely thereon a plurality of fine paths communicating with each other, and the third electrode more preferably comprises a path connecting the outer periphery of the network of the communicating paths with the exterior via the end plane of the third electrode. In this manner, the oxygen gas within the third electrode in excess can be discharged charged to the outside. The size, shape, number, etc., of the paths can be properly selected depending on conditions.

Furthermore, an air-fuel ratio sensor according to the first aspect of the present invention most preferably comprises both a first electrode provided densely thereon a plurality of fine grooves communicating with each other, and a third electrode having densely thereon a plurality of fine paths communicating with each other, with an additional path connecting the outer periphery of the network of the communicating paths with the exterior via the end plane of the third electrode, because both merits can be fully enjoyed in a single sensor.

A preferred thin film multilayered air-fuel ratio sensor according to the first aspect of the present invention comprises a sensor element having the following portions being integrated:

a portion functioning as an oxygen concentration cell type theoretical air-fuel ratio sensor comprising a porous substrate. provided thereon a first electrode, a first solid electrolyte, and a third electrode; and a portion functioning as a oxygen pump cell comprising a third electrode, a second solid electrolyte, and a fourth electrode.

A sensor according to the first aspect of the present invention may comprise an additional second electrode on the porous substrate separately from the first electrode. The sensor of this type comprises a portion functioning as an oxygen concentration cell type theoretical air-fuel ratio sensor (composed of a third electrode, a second solid electrolyte, and a fourth electrode) and a portion functioning as a limiting current type multi-range air-fuel ratio sensor (composed of a second electrode, a first solid electrolyte, and a third electrode) on a single porous substrate, in addition to the portion which functions as an oxygen pump cell.

The porous substrate for use in the thin film multilayered air-full ratio sensor according to the first aspect of the present invention may be made of a material well known in the art, for example, alumina. The size and shape of the porous substrate, as well as the type of pores and porosity may be properly selected depending on the requirements and Conditions. If desired, the sensor element may be provided with a heating means such as a heater being attached to a suitable position of the porous substrate.

The solid electrolyte for use in the thin film multilayered air-fuel ratio sensor according to the first embodiment of the present invention may be made of a material well known in the art, for example, zirconia and yttria, or a combination thereof. A solid electrolyte having a desired shape and size may be formed.

The electrode for use in the thin film multilayered air-fuel ratio sensor according to the first aspect of the present invention may be formed using a suitable paste of noble metal, for instance, a platinum paste, employing a known method such as a printing process and vapor deposition. The size, shape, and thickness of the electrode may be properly selected.

The thin film multilayered air-fuel ratio sensor according to the first aspect of the present invention may be equipped with additional means well known in the art, for example, a means for applying voltage, a means for measuring voltage or current, and a heating means such as a heater.

Preferably, the outer surface of the sensor element of the thin film multilayered air-fuel ratio sensor according to the first aspect of the present invention is entirely covered with a coating layer carrying a predetermined amount of a catalytic metal, such as a noble metal catalyst (oxidizing catalyst) including platinum, rhodium, and palladium. In this manner, the sensor characteristics can be ameliorated by completely combusting the unburnt gas remaining in the exhaust gas to eliminate unfavorable influences cast by them. The type of the catalyst, the content thereof in the coating layer, the thickness of the coating layer, and the coating material are properly selected, and such parameters can be used either alone or in combination of two or more selected therefrom.

In the preferred thin film multilayered air-fuel ratio sensor according to the first aspect of the present invention, the surface portion of the porous substrate in contact with the first electrode (and also the portion in contact with the second electrode in case a second electrode is provided) preferably comprises irregularities having peaks with a distance of 1 µm or more between the neighboring peaks. In this manner, an oxygen concentration cell type theoretical air-fuel ratio sensor and/or a limiting current type multi-range air-fuel ratio sensor further improved in performance can be realized.

Referring to a thin film multilayered air-fuel ratio sensor according to a second aspect of the present invention, a second solid electrolyte having an opening is provided on the third electrode incorporating a space between the first and the second solid electrolytes. This is the feature differing from the air-fuel ratio sensor according to the first aspect of the present invention. The size (volume) and the shape of the space between the first and the second solid electrolytes are properly selected. The space may be filled with a suitable porous material, such as a ceramic foam. When an excess amount of oxygen is supplied from the oxygen pump cell constructed by the fourth electrode, the second solid electrolyte, and the fifth electrode, the excess oxygen gas is discharged to the outside from the opening provided on the second solid electrolyte. Thus, the oxygen gas partial pressure can be always maintained at an optimal value.

The size, shape, and number of the opening provided on the second solid electrolyte can be properly selected to obtain a sensor element having the desired performance. A pinhole, for example, may be provided as the opening.

In the sensor according to the second aspect of the present invention again, a second electrode may be additionally provided on the porous substrate independent of the first electrode. In this case, the sensor comprises a portion functioning as an oxygen concentration cell type theoretical air-fuel ratio sensor and a portion functioning as a limiting current type multi-range air-fuel ratio sensor on a single porous substrate, in addition to the portion which functions as an oxygen pump cell.

Other constituent elements and additional means to be provided to the thin film multilayered air-fuel ratio sensor according to the second aspect of the present invention are the same as those described above in the case of a thin film multilayered air-fuel ratio sensor according to the first aspect of the present invention.

In the thin film multilayered air-fuel ratio sensor according to the present invention, oxygen ions are supplied forcibly to the sensor element using an oxygen pump function and by dissociating oxygen from water vapor and carbon dioxide being present in the exhaust gas discharged upon combustion of fuel in a motorcar engine. This is the very point which-differs from the conventional zirconia theoretical air-fuel ratio sensor and zirconia limiting current type multi-range air-fuel ratio sensor having a path connected to one of the electrodes to supply oxygen at high concentration depending on the natural diffusion of air. The sensor according to the present invention comprises under an oxygen pump cell, an oxygen concentration cell and/or a limiting current cell formed on a porous substrate using a thin film deposition technology. Thus, a low-power consuming and quick-response sensor which can be subjected to rapid heating and quick elevation of temperature can be implemented. The sensor thereby allows high precision measurement of theoretical air-fuel ratio and multi-range air-fuel ratio.

The present invention is illustrated in greater detail referring to non-limiting examples below. It should be understood, however, that the present invention is not to be construed as being limited thereto.

EXAMPLE 1

Oxygen Concentration Cell Type Theoretical Air-fuel Ratio Sensor According to First Aspect of Invention Referring to FIG. 1, a sensor according to EXAMPLE 1 of the present invention is described below. The present sensor comprises a porous substrate 1 made of, for example, alumina, and a first electrode 2, a first solid electrolyte 3, and a third electrode 4 formed thereon in this order. The first solid electrolyte 3 completely covers the surface of the first electrode 2 inclusive of its surroundings. The third electrode 4 further covers completely the surface of the first solid electrolyte 3 inclusive of its surroundings. A second solid electrolyte 5 and a fourth electrode 6 are formed in this order further on the third electrode 4, provided that the second solid electrolyte 5 and the fourth electrode 6 are arranged as such that the peripheral portion of the third electrode 4 may be left exposed. The first electrode 2, the third electrode 4, and the fourth electrode 6 are each made of a gas-permeable porous platinum. Those electrodes can be formed by applying a platinum paste using a printing process. The first solid electrolyte 3 and the second solid electrolyte 5 are formed using a gas-impermeable dense solid electrolyte having oxygen ion conductivity (zirconia is used in this case).

A heater 7 is provided on the back of the porous substrate 1. The heater 7 is connected to a heating means 8. Suitable materials for the heater 7 include noble metals such as platinum, rhodium, palladium, etc., alloys thereof, and heat-resistant electrically conductive materials comprising SiC, W, Re, Mo, etc. Platinum is used in this example.

A means 9 for applying voltage is further provided to apply a positive voltage to the third electrode 4 with respect to the fourth electrode 6. The structure is shown in FIG. 1. A means 10 for measuring the voltage (potential difference) of the third electrode 4 with respect to the first electrode 2 is also provided.

On applying a positive voltage to the third electrode 4 with respect to the fourth electrode 6, an oxygen pump functions in this portion inclusive of the second solid electrolyte 5 to transfer the oxygen ions from the fourth electrode 6 side to the third electrode 4 side. Under an atmosphere of lean air-fuel ratio, the oxygen remaining in the atmosphere is supplied to the fourth electrode 6 by gas diffusion. Since there is no sufficient oxygen left in a rich air-fuel ratio atmosphere, water vapor and carbon dioxide supplied to the fourth electrode 6 from the atmosphere by gas diffusion undergo dissociation inside the fourth electrode 6 to form oxygen ions. Thus, the resulting oxygen ions are transferred in the same manner as in the previous process. The thus transferred oxygen ions are converted into oxygen gas at the boundary between the second solid electrolyte 5 and the third electrode 4. In this manner, an oxygen rich state is maintained inside the porous third electrode 4 irrespective of the atmospheric condition, i.e., irrespective of whether the atmosphere is in a lean or rich air-fuel ratio.

Figure 2:
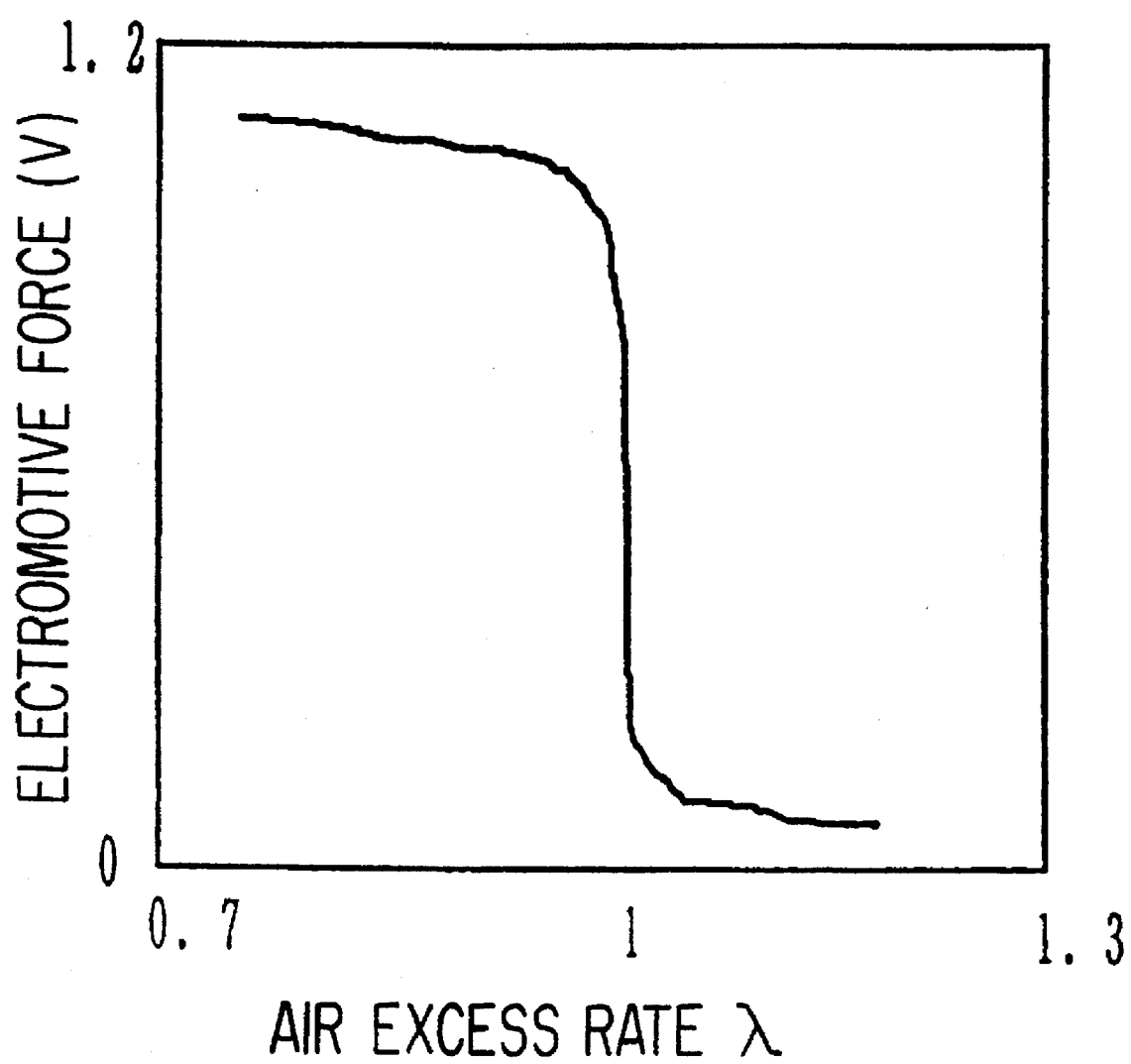
FIG. 2 is a graph showing the electromotive force characteristics of an air-fuel ratio sensor according to EXAMPLE 1 of the present invention.

The portion comprising the first electrode 2, the first solid electrolyte 3, and the third electrode 4 functions as an oxygen concentration cell type air-fuel ratio sensor portion to measure the theoretical air-fuel ratio from the electromotive force. Then, the electromotive force of the oxygen concentration cell type air-fuel ratio sensor portion was measured taking the air ratio in the exhaust gas surrounding the sensor as a parameter to obtain a characteristic curve as shown in FIG. 2.

Since the outer periphery of the porous third electrode 4 is connected with the outside of the sensor, oxygen being supplied in excess can be discharged from the outer periphery to the outside. Thus, measurement can be performed without any obstruction. The oxygen gas inside the first electrode 2 is discharged into the porous substrate 1.

EXAMPLE 2

Oxygen Concentration Cell Type Theoretical Air-fuel Ratio Sensor According to First Aspect of Invention Referring to FIG. 3, a sensor according to EXAMPLE 2 of the present invention is described below. The present sensor has essentially the same structure as that of the sensor described in EXAMPLE 1, except that fine grooves 11 communicating with each other are provided densely on the portion of a first electrode 2 in contact with a porous substrate 1. In general, a theoretical air-fuel ratio sensor is equipped with a platinum electrode. However, platinum exhibits an insufficient durability when subjected to repeated oxidation and reduction. Thus, by covering the surface of the platinum electrode with a porous layer to control the amount of diffused gas to reach the surface of the electrode from the atmosphere, the degradation of the electrode can be suppressed, and a long term durability can be imparted thereto. It can be seen therefore that it is effective to lower the amount of gas diffusion using a porous substrate 1 having a high diffusion resistance. However, the use of such a substrate reversely generates a portion in the surface of the first electrode 2 where oxygen is insufficiently supplied (ineffective portion). In other words, a portion of long transient response is generated on the first electrode 2. Then, the electromotive force of the normal portion having a short transient response and that of the abnormal portion having a long transient response mutually influence to yield, as a whole, a slow response. Such an obscure characteristic is unsuited for a sensor for controlling the air-fuel ratio. The present invention provides a solution to such a problem.

The grooves 11 facilitates oxygen gas diffusion inside the surface of the first electrode 2 to thereby control the in-plane oxygen concentration distribution to a low level. In this manner, the generation of the in-plane portion supplied insufficiently with oxygen in the surface of the first electrode 2 (ineffective portion), i.e., the portion having a long transient response, can be suppressed. Thus, the in-plane transient response of the electrode can be made uniform. Conclusively, a sensor having favorable durability and improved in long term durability can be implemented while preventing slow response unsuited for an air-fuel ratio sensor from occurring.

Figure 3:
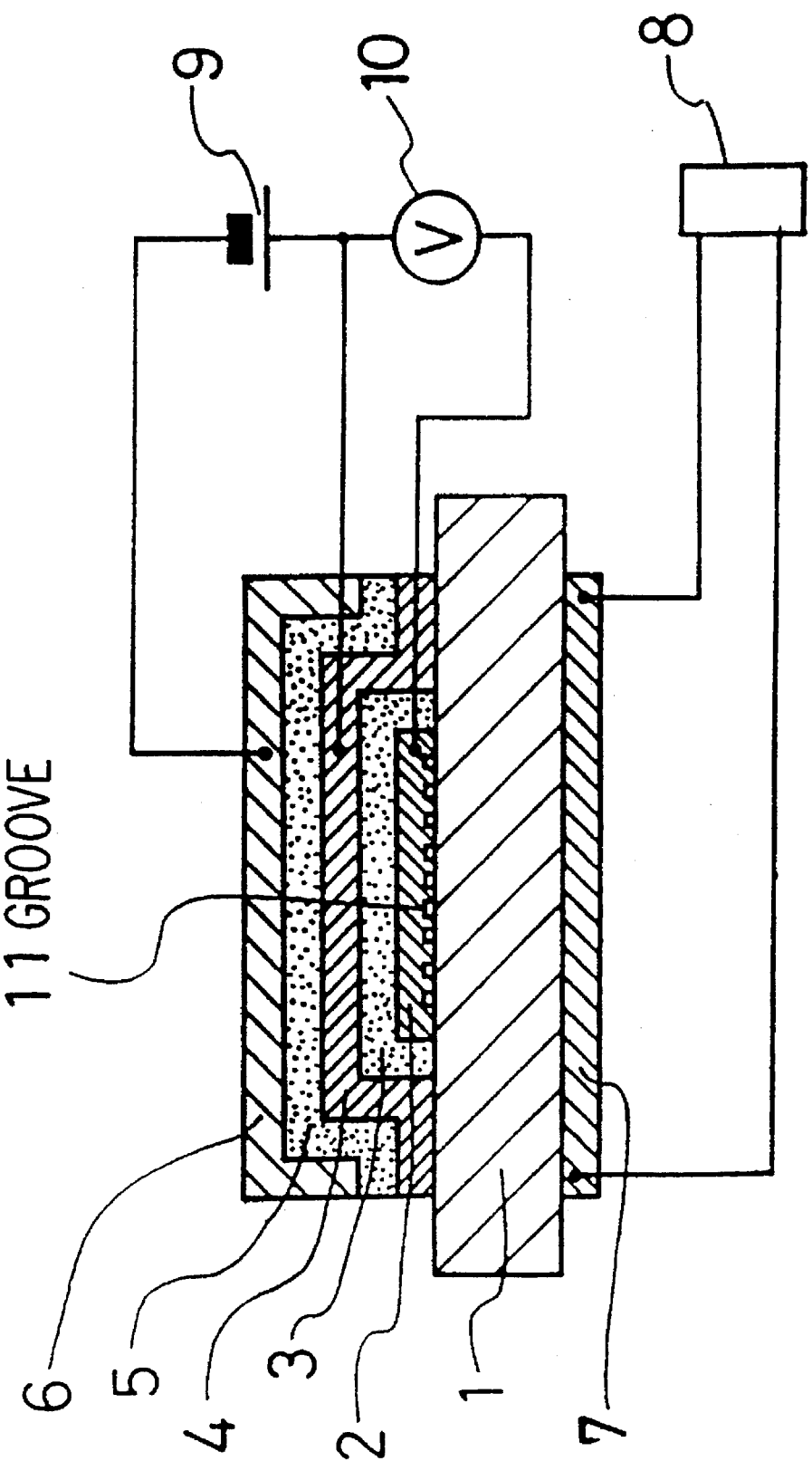
FIG. 3 is a schematic view illustrating an air-fuel ratio sensor according to EXAMPLE 2 of the present invention.
Figure 4:
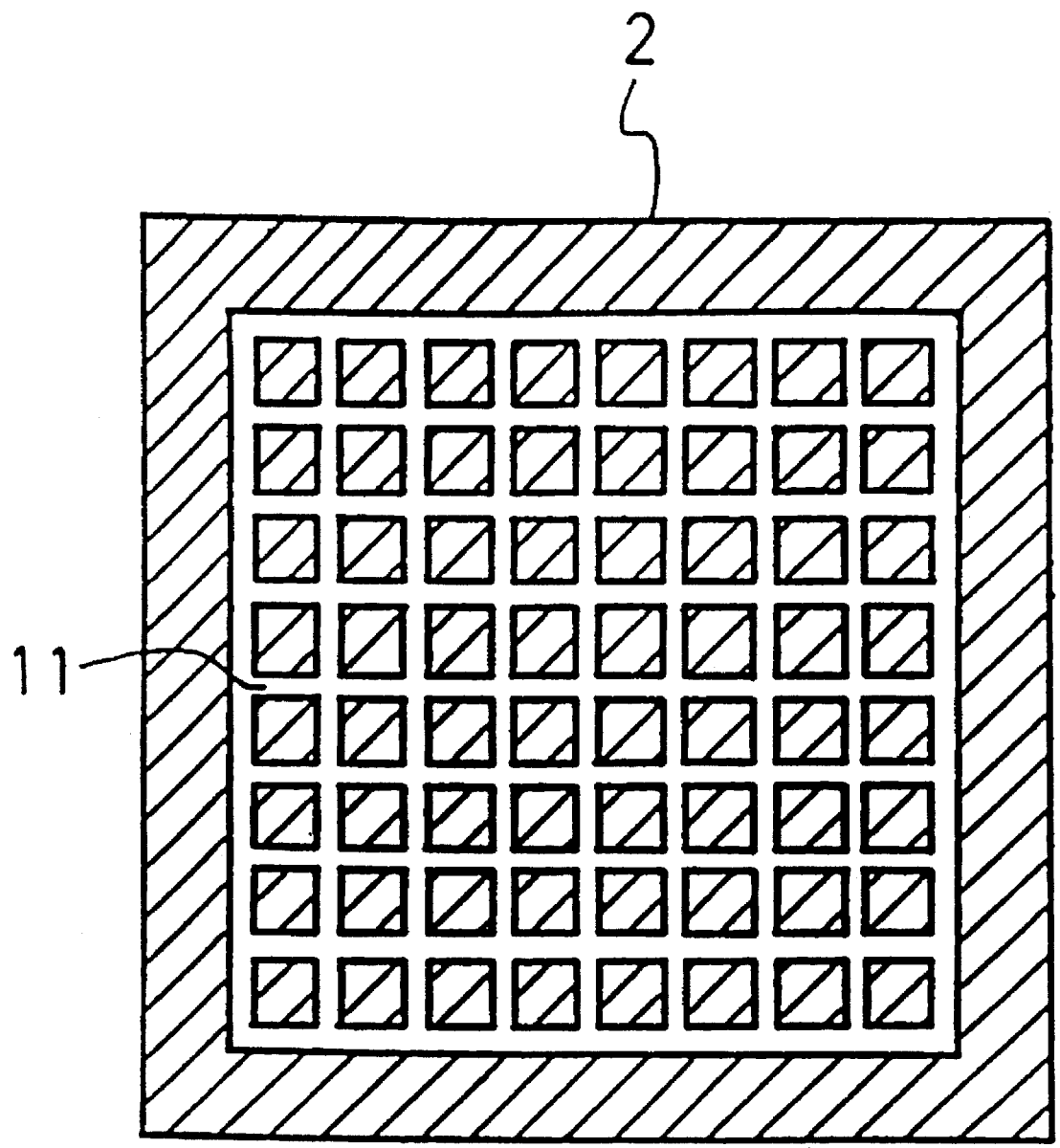
FIG. 4 is a plan view of a first electrode of the air-fuel ratio sensor shown in FIG. 3.

FIG. 4 shows a plan view of the first electrode 2 given in FIG. 3. In the present example, the grooves 11 are cut into a lattice having a predetermined spacing.

EXAMPLE 3

Oxygen Concentration Cell Type Theoretical Air-fuel Ratio Sensor According to First Aspect of Invention Referring to FIG. 5, a sensor according to EXAMPLE 3 of the present invention is described below. The present sensor has essentially the same structure as that of the sensor described in EXAMPLE 1, except that fine paths 12 communicating with each other are provided densely in the inside of a third electrode 4, and that additional paths 13 for communicating the peripheral portion of the path network with the outside are provided on the third electrode 4 in such a manner that they may be connected via the outer peripheral end of the third electrode 4.

When the pressure inside the third electrode 4 is elevated by operating the oxygen pump, the oxygen gas in excess is discharged to the outside through the fine paths 12 and a path 13. In this manner, the elevation of pressure inside the second electrode 4 can be suppressed.

Figure 5:
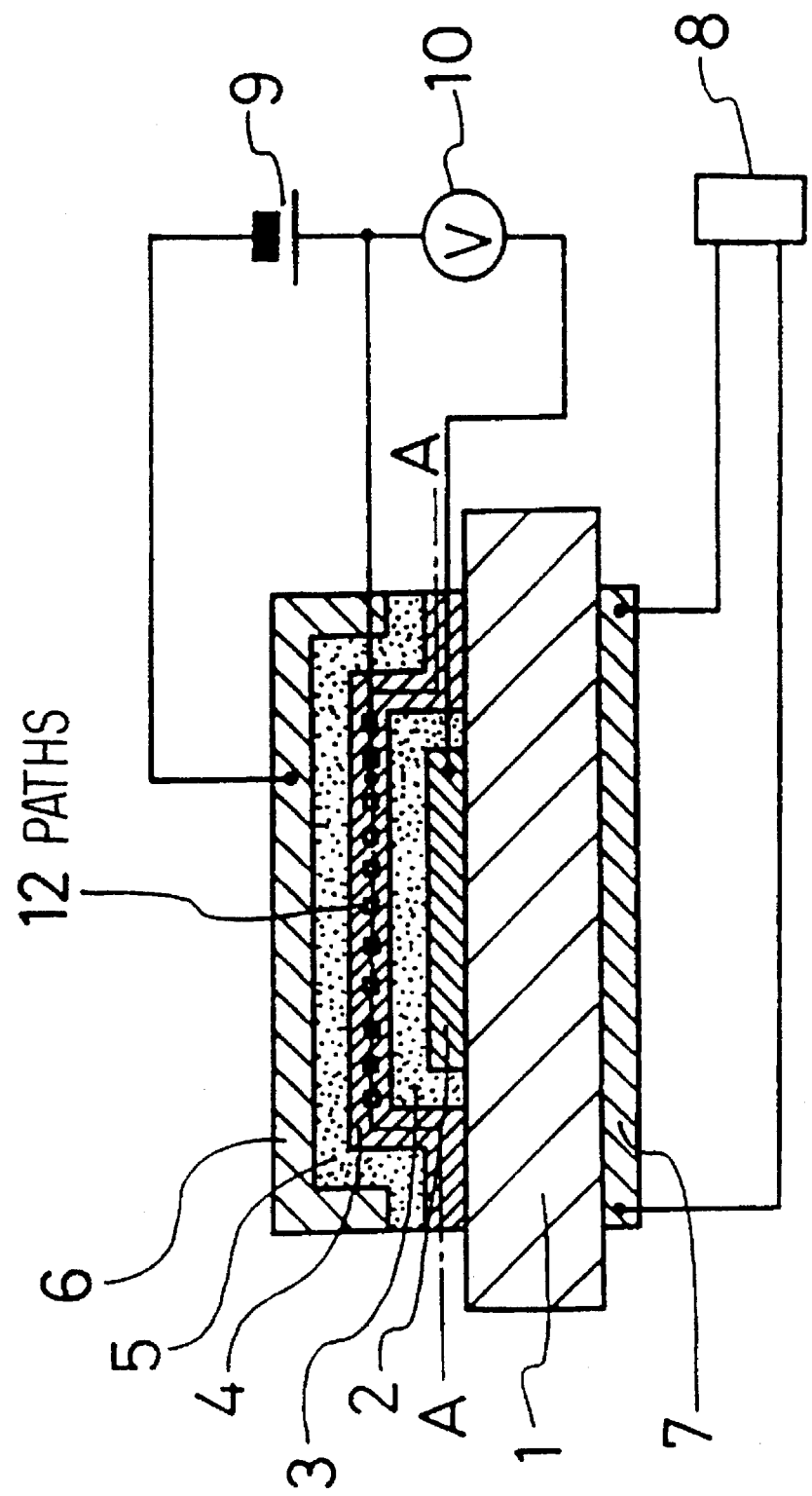
FIG. 5 is a schematic view illustrating an air-fuel ratio sensor according to EXAMPLE 3 of the present invention.
Figure 6:
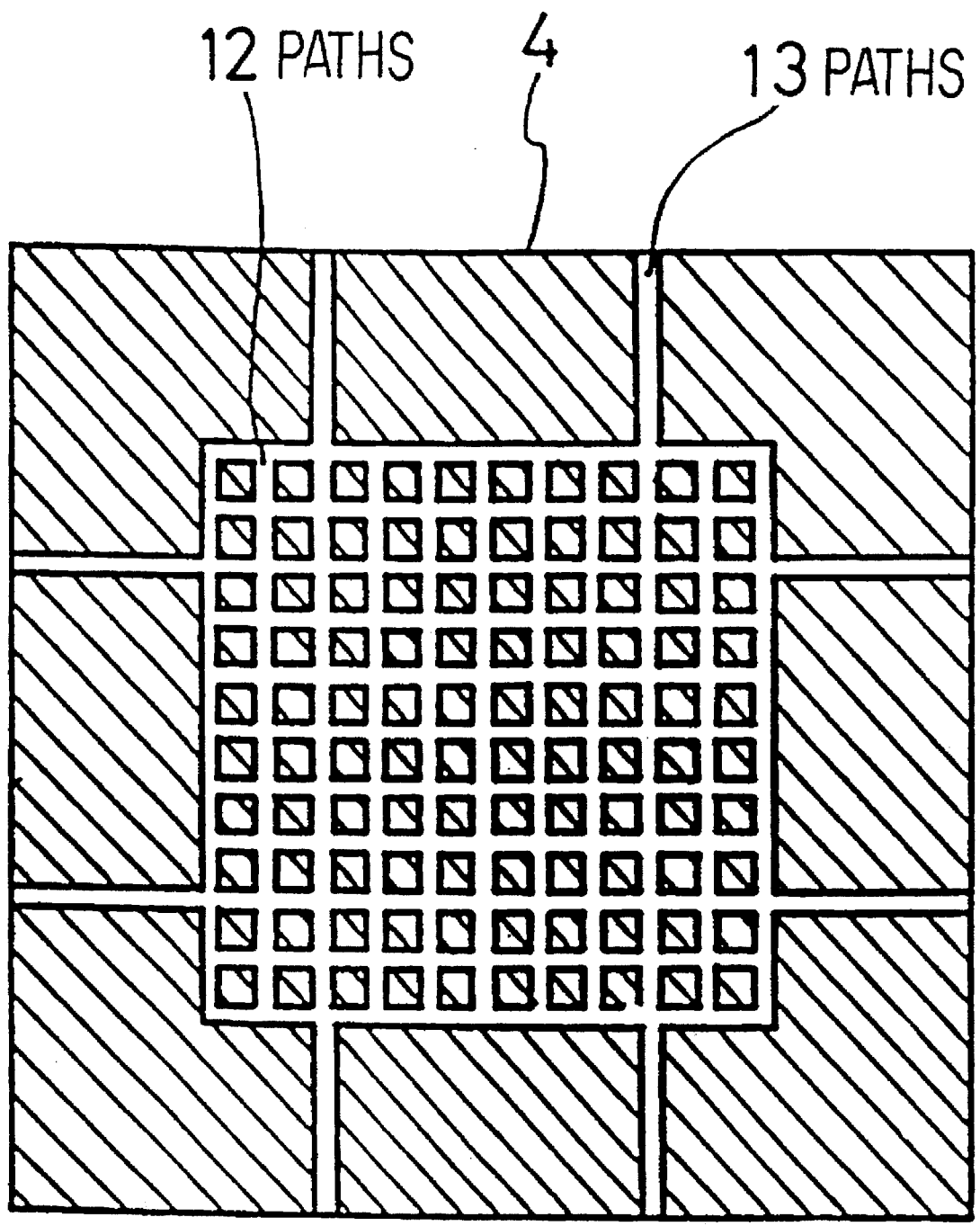
FIG. 6 is a plan view of a third electrode of the air-fuel ratio sensor taken along A—A line in FIG. 5.

FIG. 6 is a plan view of the third electrode 4 viewed along line A—A given in FIG. 5. In the present example, the paths 12 are cut into a lattice having a predetermined spacing. The paths 13 are provided along the vertical and transversal directions on the outer periphery of the paths 12 to connect the outer periphery of the paths 12 with the outside.

EXAMPLE 4

Oxygen Concentration Cell Type Theoretical Air-fuel Ratio Sensor According to First Aspect of Invention Referring to FIG. 7, a sensor according to EXAMPLE 4 of the present invention is described below. The present sensor has essentially the same structure as that of the sensor described in EXAMPLE 1, except that fine grooves 11 communicating with each other are provided densely on the portion of a first electrode 2 in contact with a porous substrate 1 in a similar manner as in EXAMPLE 2, and that fine paths 12 communicating with each other are provided densely on a third electrode 4, with an additional paths 13 for communicating the peripheral portion of the path network with the outside being provided on the third electrode 4, in such a manner that they may be connected via the outer peripheral end of the third electrode 4.

It can be seen therefore that the sensor of the present example possesses both advantages of the sensors described in EXAMPLE 2 and EXAMPLE 3.

Figure 7:
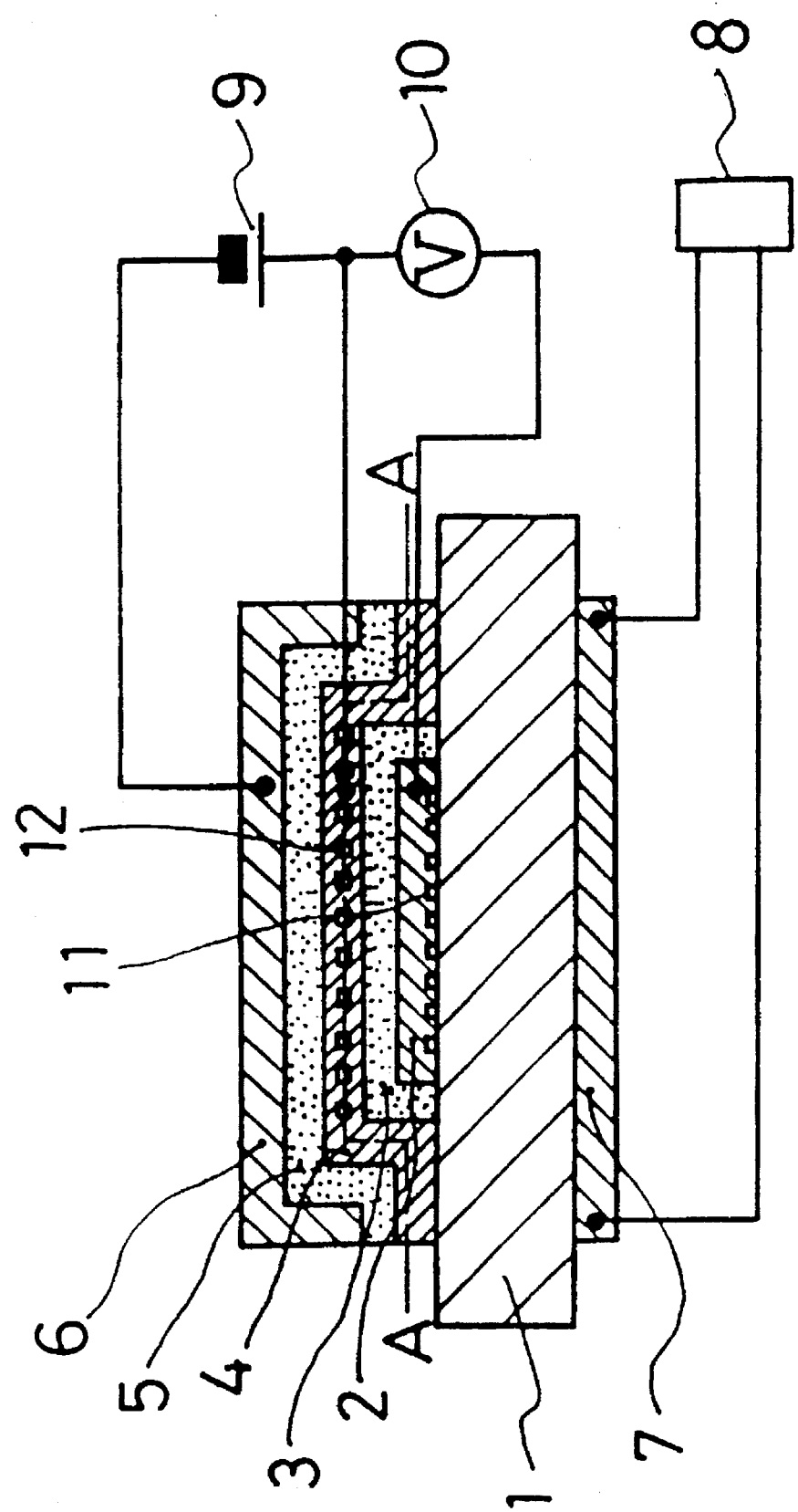
FIG. 7 is a schematic view illustrating an air-fuel ratio sensor according to EXAMPLE 4 of the present invention.
Figure 8:
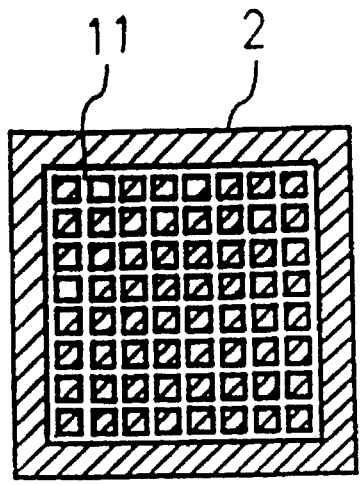
FIG. 8 is a plan view of a first electrode of the air-fuel ratio sensor shown in FIG. 7.
Figure 9:
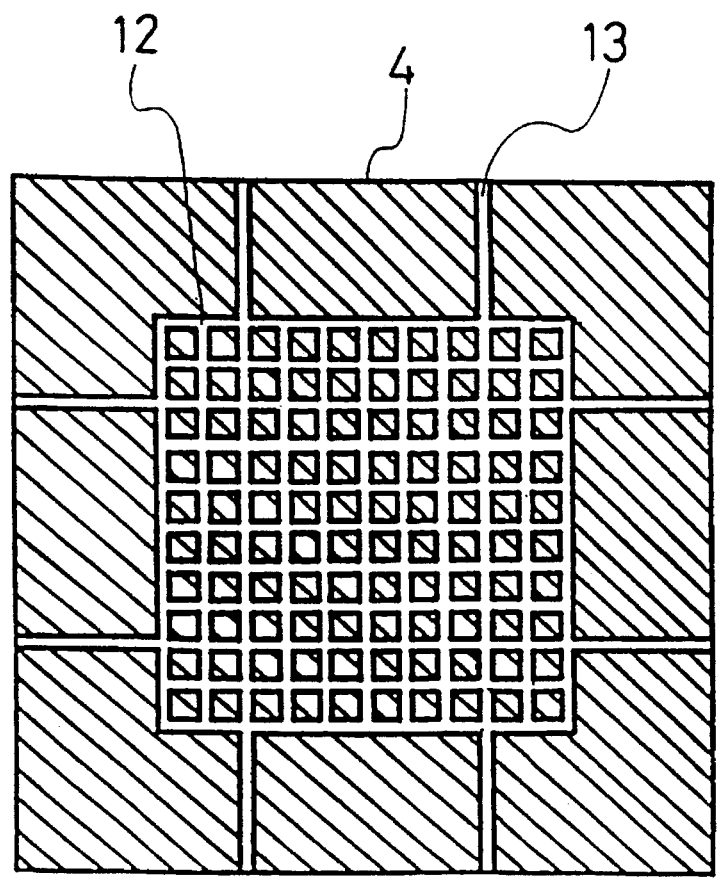
FIG. 9 is a plan, view of a third electrode of the air-fuel ratio sensor taken along A—A line in FIG. 7.

FIG. 8 is a plan view of the first electrode 2 given in FIG. 7. In the present example, the grooves 11 are cut into a lattice having a predetermined spacing. FIG. 9 is a plan view of the third electrode 4 viewed along line A—A given in FIG. 7. In the present example, the paths 12 are cut into a lattice having a predetermined spacing. The paths 13 are provided along the vertical and transversal directions on the outer periphery of the paths 12 to connect the outer periphery of the paths 12 with the outside.

EXAMPLE 5

Figure 10:
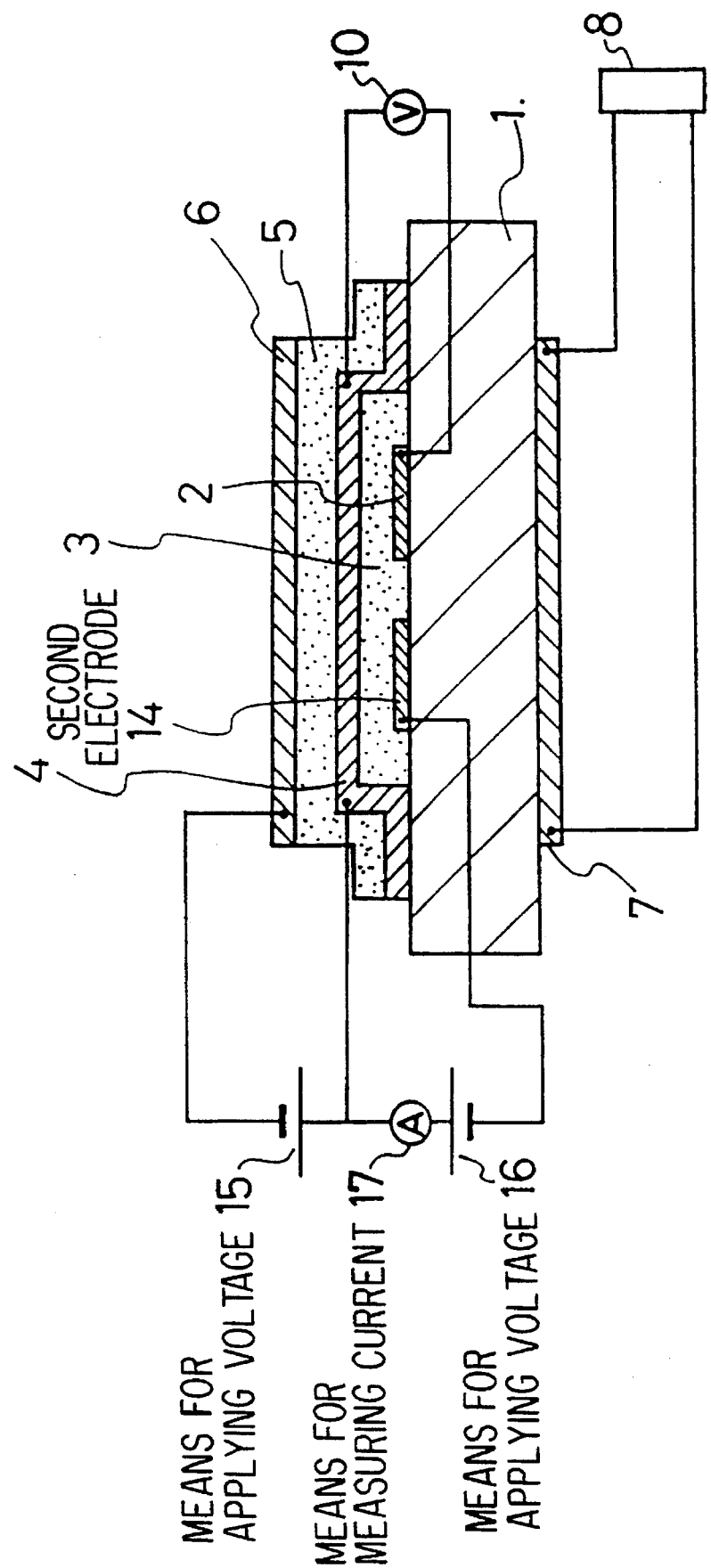
FIG. 10 is a schematic view illustrating an air-fuel ratio sensor according to EXAMPLE 5 of the present invention.

Oxygen Concentration Cell Type Theoretical Air-fuel Ratio Sensor and Limiting Current Type Multi-range Air-fuel Ratio Sensor According to First Aspect of Invention Referring to FIG. 10, a sensor according to EXAMPLE 5 of the present invention is described below. The present sensor comprises a porous substrate 1 made of, for example, alumina. The porous substrate comprises surface irregularities having peaks being distributed in such a manner that the distance between the neighboring peaks is 1 μm or more. The porous substrate 1 comprises formed thereon in this order, a first electrode 2, a second electrode 14 arranged in parallel with the first electrode, a first solid electrolyte 3, and a third electrode 4. The first solid electrolyte 3 completely covers the surface of the first electrode 2 and the second electrode 14 inclusive of their surroundings. The third electrode 4 further covers completely the surface of the first solid electrolyte 3 inclusive of its surroundings. A second solid electrolyte 5 and a fourth electrode 6 are formed in this order on the third electrode 4, provided that the second solid electrolyte 5 and the fourth electrode 6 are arranged as such that the peripheral portion of the third electrode 4 may be left exposed. The first electrode 2, the second electrode 14, the third electrode 4, and the fourth electrode 6 are each made of a gas-permeable porous platinum. Those electrodes can be formed, for example, by applying a platinum paste using a printing process. The first solid electrolyte 3 and the second solid electrolyte 5 are formed using a gas-impermeable dense solid electrolyte having oxygen ion conductivity (zirconia is used in this case).

A heater 7 is provided on the back of the porous substrate 1. The heater 7 is connected to a heating means 8. Suitable materials for the heater 7 include noble metals such as platinum, rhodium, palladium, etc., alloys thereof, and heat-resistant electrically conductive materials comprising SiC, W, Re, Mo, etc. Platinum is used in this example.

A means 15 for applying voltage is further provided to apply a positive voltage to the third electrode 4 with respect to the fourth electrode 6. The structure is shown in FIG. 10. A means 16 for applying a positive voltage to the third electrode 4 with respect to the second electrode 14 is also provided. A means 17 for measuring the current is established. A means 10 for measuring the electromotive force between the third electrode 4 and the first electrode 2 is further installed.

On applying a positive voltage to the third electrode 4 with respect to the fourth electrode 6, an oxygen pump functions in this portion inclusive of the second solid electrolyte 5 to transfer the oxygen ions from the fourth electrode 6 side to the third electrode 4 side. Under an atmosphere of lean air-fuel ratio, the oxygen remaining in the exhaust gas is ionized in the fourth electrode 6 to form oxygen ions. Since there is no sufficient oxygen left in a rich air-fuel ratio atmosphere, water vapor and carbon dioxide supplied to the fourth electrode 6 from the atmosphere by gas diffusion undergo dissociation inside the fourth electrode 6 to form oxygen ions. Thus, the resulting oxygen ions are transferred to the third electrode 4 through the second solid electrolyte 5 by ion conduction, and are converted into oxygen gas at the boundary between the second solid electrolyte 5 and the third electrode 4. In this manner, an oxygen rich state is maintained inside the porous third electrode 4 irrespective of the atmospheric condition, i.e., irrespective of whether the atmosphere is in a lean or rich air-fuel ratio.

Figure 11:
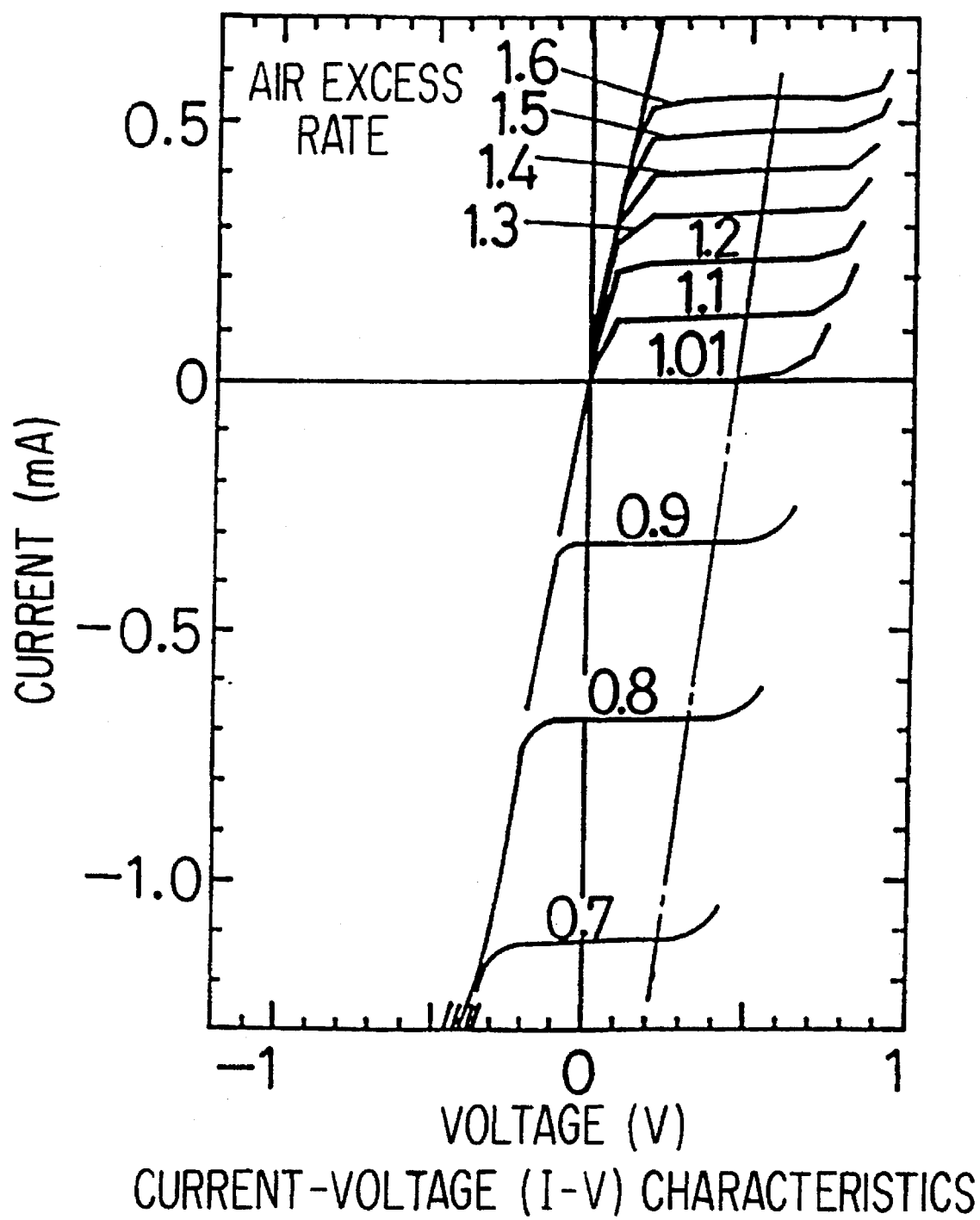
FIG. 11 is a graph showing a current-voltage (I–V) characteristics for a limiting current type multi-range air-fuel ratio sensor portion of an air-fuel ratio sensor according to EXAMPLE 5 of the present invention.
Figure 12:
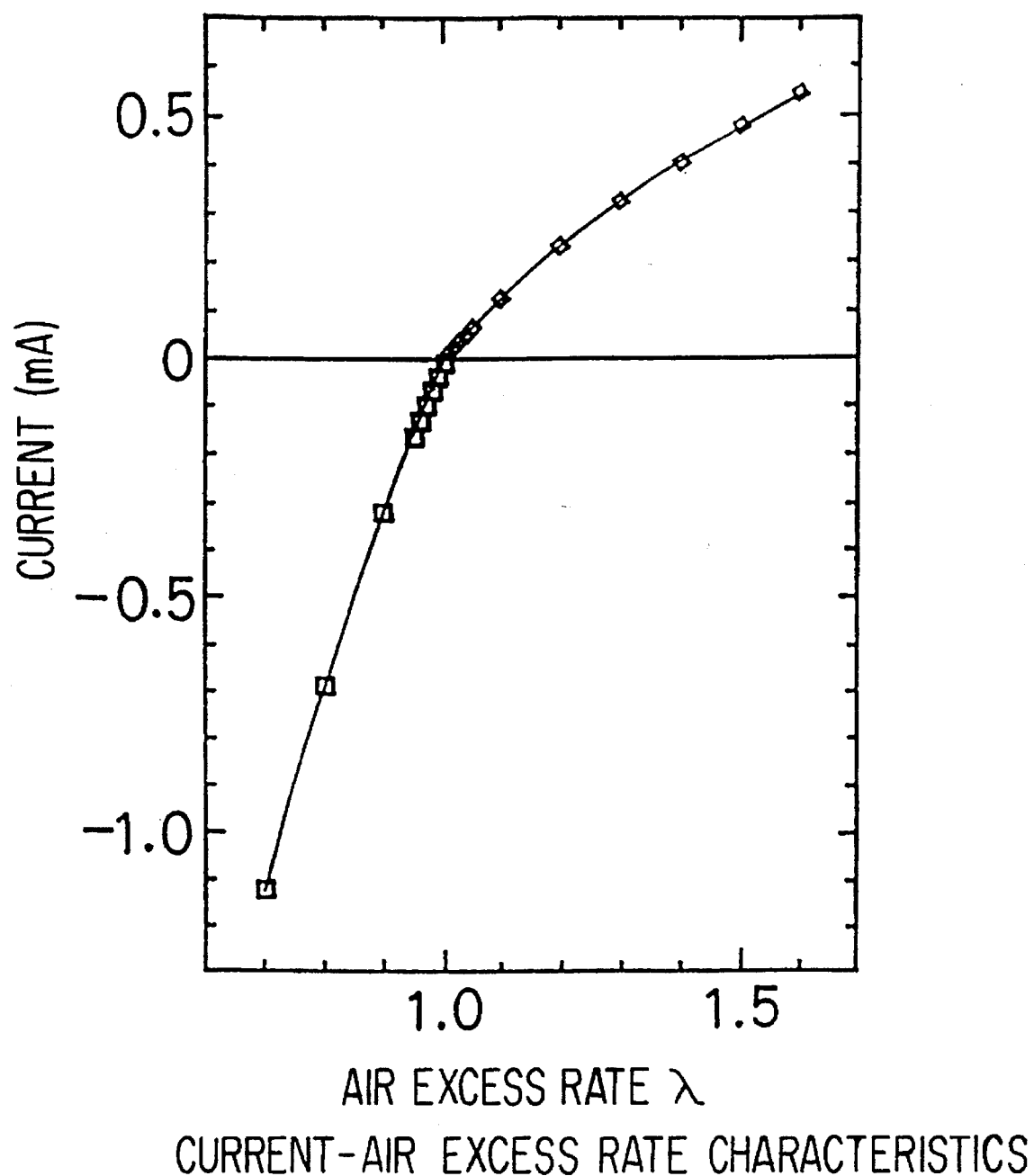
FIG. 12 is a graph showing observed current upon applying the applied voltage shown with dash-dotted line in the graph of FIG. 11 for an air-fuel ratio sensor according to EXAMPLE 5 of the present invention.

The portion comprising the second electrode 14, the first solid electrolyte 3, and the third electrode 4 functions as a limiting current type multi-range air-fuel ratio sensor to provide the air-fuel ratio from the limiting current. Then, the current-voltage (I–V) characteristics of the limiting current type multi-range air-fuel ratio sensor was measured taking the air excess ratio as a parameter to obtain a characteristic curve as shown in FIG. 11. Furthermore, voltage shown with dash-dot line given in FIG. 11 was applied to the sensor to obtain observed current as plotted in FIG. 12.

On the other hand, the portion comprising the first electrode 2, the first solid electrolyte 3, and the third electrode 4 functions as an oxygen concentration cell type theoretical air-fuel ratio sensor to measure the theoretical air-fuel ratio from the abrupt change in electromotive force. Then, the electromotive force of the oxygen concentration cell type air-fuel ratio sensor portion was measured taking the air excess ratio as a parameter to obtain a characteristic curve similar to that shown in FIG. 2.

Figure 22:
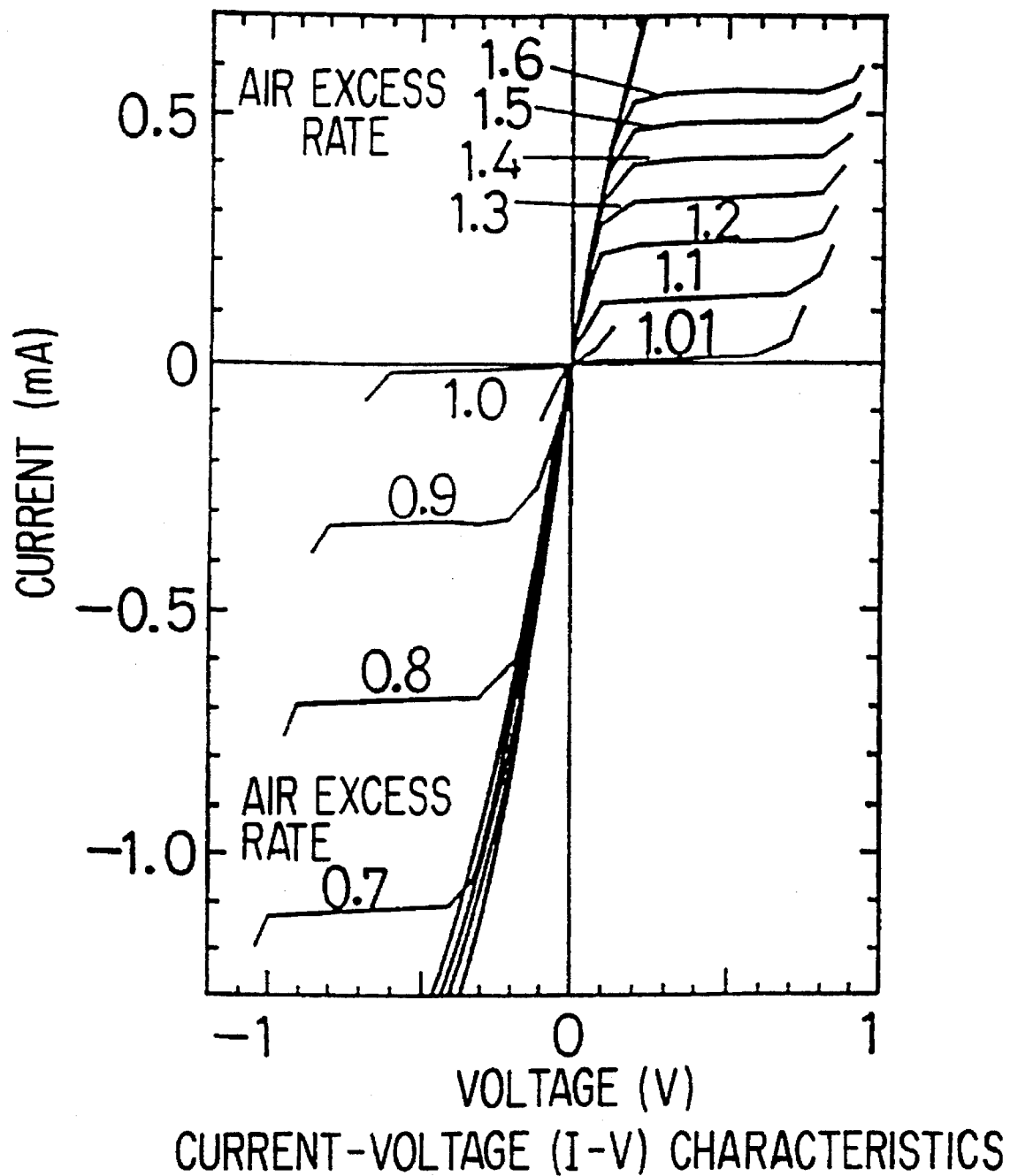
FIG. 22 is a graph showing a current-voltage (I–V) characteristics for a limiting current type multi-range air-fuel ratio sensor portion of a prior art air-fuel ratio sensor.
Figure 23:
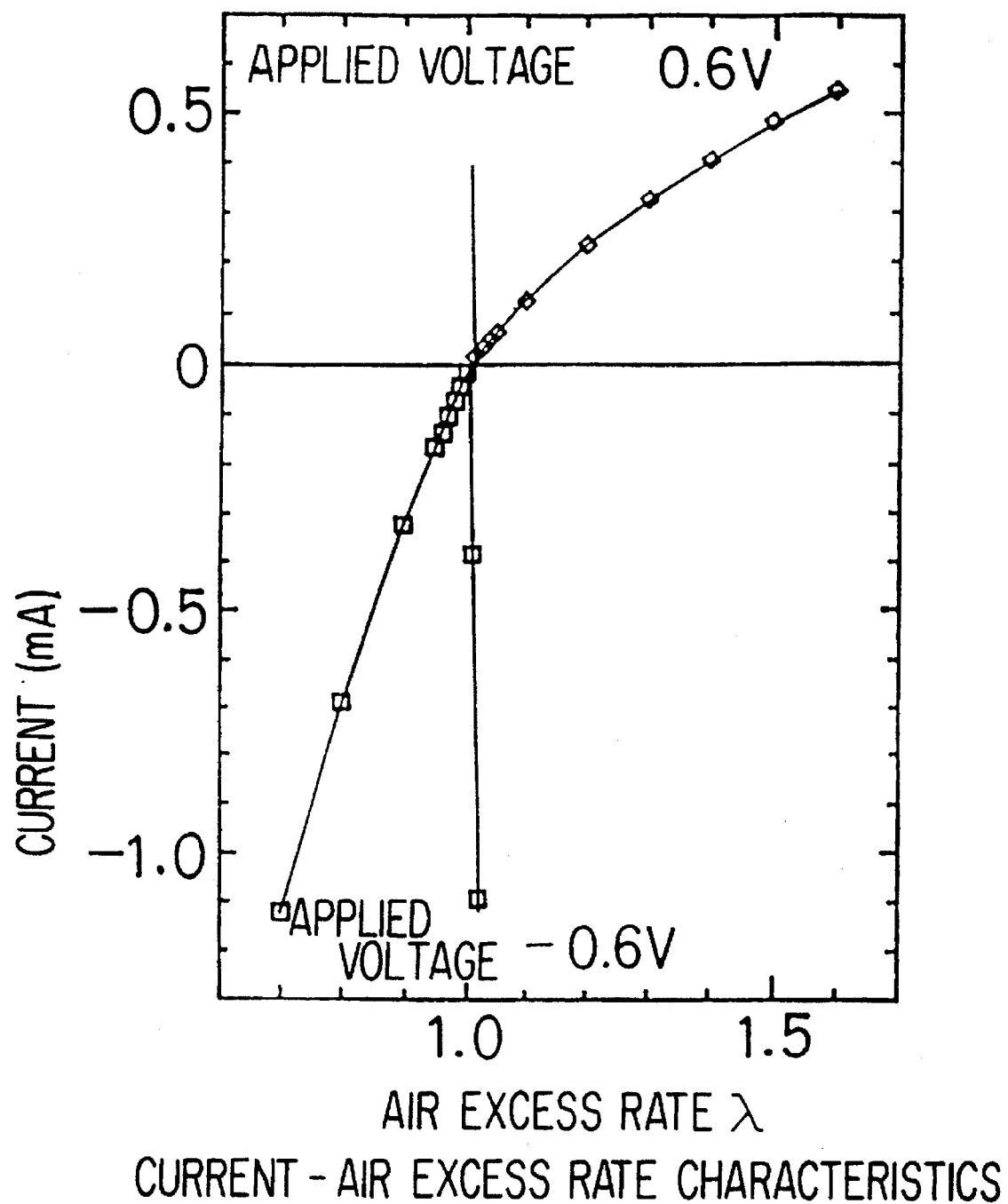
FIG. 23 is a graph showing observed current upon applying a predetermined voltage for a prior art air-fuel ratio sensor.

The characteristics of a prior art air-fuel ratio sensor are shown in FIGS. 22 and 23 to compare that of the air-fuel ratio sensor portion of the sensor of EXAMPLE 5. FIG. 22 corresponds to FIG. 11, and FIG. 23 corresponds to FIG. 12. It can be seen by comparing FIGS. 22 and 23 with FIGS. 11 and 12, respectively, that, in contrast to the prior art air-fuel ratio which exhibits a limit current characteristics in the third quadrant under a fuel-rich atmosphere (i.e., an atmosphere having an air ratio lower than 1), the present sensor yields the limit current characteristics in the fourth quadrant.

This result signifies that a conventional air-fuel ratio sensor required the polarity to be switched depending on the air ratio of the atmosphere. More specifically, a positive voltage should be applied to the prior art sensor under an atmosphere having an air excess ratio higher than 1 (i.e., under a fuel lean atmosphere), whereas a negative voltage is required under an atmosphere having an air excess ratio lower than 1 (i.e., under a fuel rich atmosphere). The sensor according to the present invention can be operated while maintaining a positive applied voltage without switching the polarity.

Accordingly, there is no need of providing a separate detecting means to see whether the atmosphere is in a fuel-lean or fuel-rich state.

Furthermore, since the polarity of applied voltage need not be switched, the noise on the output signal attributed to the switching of polarity is also eliminated.

The oxygen inlet which were necessary for a prior art multi-range air-fuel ratio sensor can be omitted in the air-fuel ratio sensor portion of the sensor according to the present example. By adding an electrochemical cell which functions as an oxygen pump on the third electrode 4, oxygen can be sufficiently supplied to allow the sensor to function as an equivalent to a prior art multi-range air-fuel ratio sensor.

EXAMPLE 6

Figure 13:
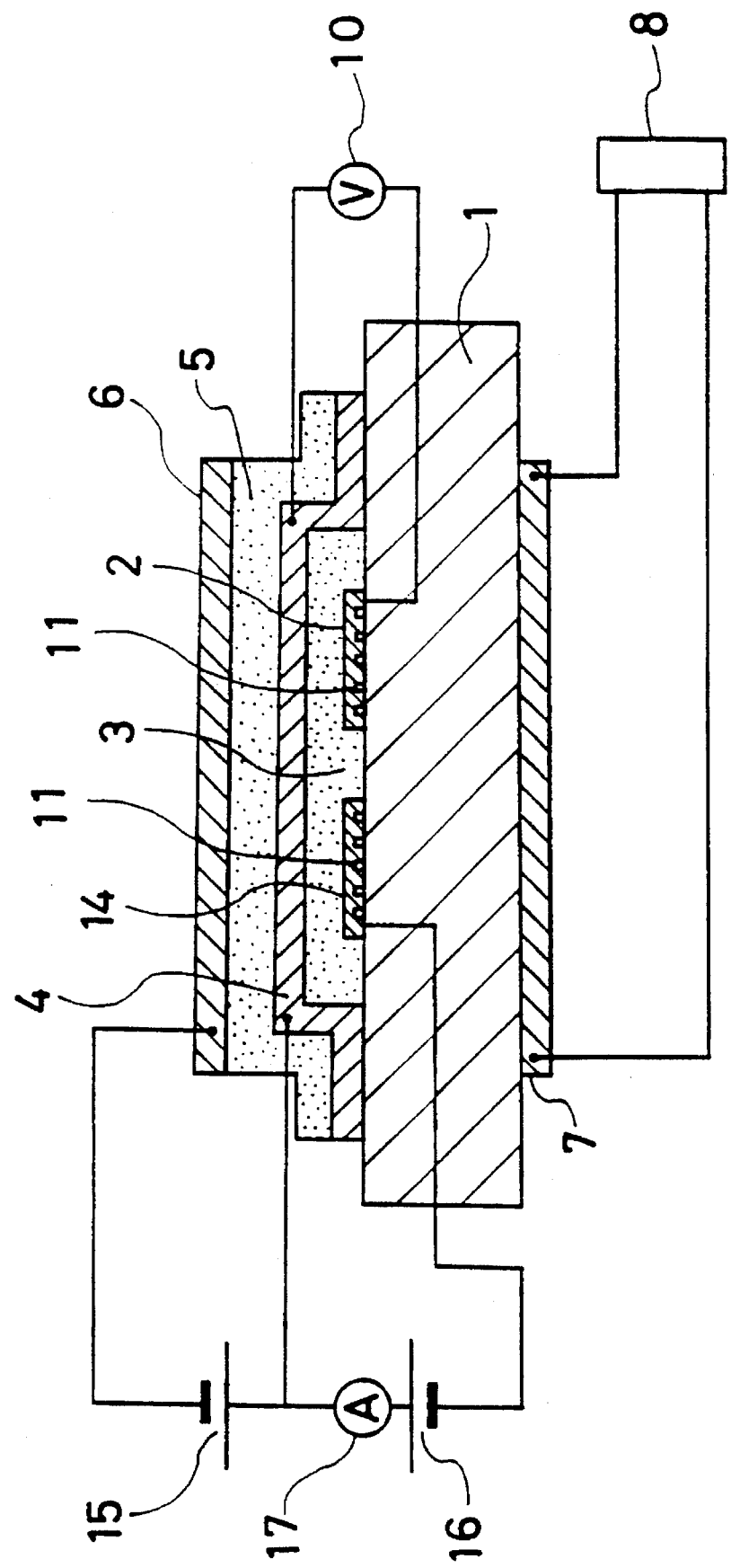
FIG. 13 is a schematic view illustrating an air-fuel ratio sensor according to EXAMPLE 6 of the present invention.

Oxygen Concentration Cell Type Theoretical Air-fuel Ratio Sensor and Limiting Current Type Multi-range Air-fuel Ratio Sensor According to First Aspect of Invention Referring to FIG. 13, a sensor according to EXAMPLE 6 of the present invention is described below. The present sensor has essentially the same structure as that of the sensor described in EXAMPLE 5, except that fine grooves 11 communicating with each other are provided densely on the portion of a first electrode 2 and a second electrode 14 in contact with a porous substrate 1. When the current per unit area of the electrode (i.e., current density) is increased in an oxygen sensor, in general, the resistance of the electrode happens to greatly influence and thereby impair the initial characteristics of the sensor. Moreover, such an influence also negatively affects long term stability of the sensor. It can be seen therefore that the use of a porous substrate 1 having a high diffusion resistance is effective to lower the amount of gas diffusion. However, the use of such a substrate reversely generates a portion in the surface of the first electrode 2 and the second electrode 14 where oxygen is insufficiently supplied (ineffective portion). The present invention provides a solution to such a problem.

The grooves 11 facilitates oxygen gas diffusion inside the surface of the first electrode 2 and the second electrode 14 to thereby control the in-plane oxygen concentration distribution to a low level. In this manner, the generation of the in-plane portion supplied insufficiently with oxygen in the surface of the first electrode 2 and the second electrode 14 can be suppressed. Thus, such a measure prevents the resistance inside the electrodes from increasing. Conclusively, a sensor having favorable initial characteristics with the lowering of current density and considerably improved in long term durability can be implemented.

The plan view of the grooves 11 provided on the first electrode 2 and the second electrode 14 of the sensor of EXAMPLE 6 is the same as that shown in FIG. 4. In the present example, the grooves 11 are cut into a lattice having a predetermined spacing.

EXAMPLE 7

Figure 14:
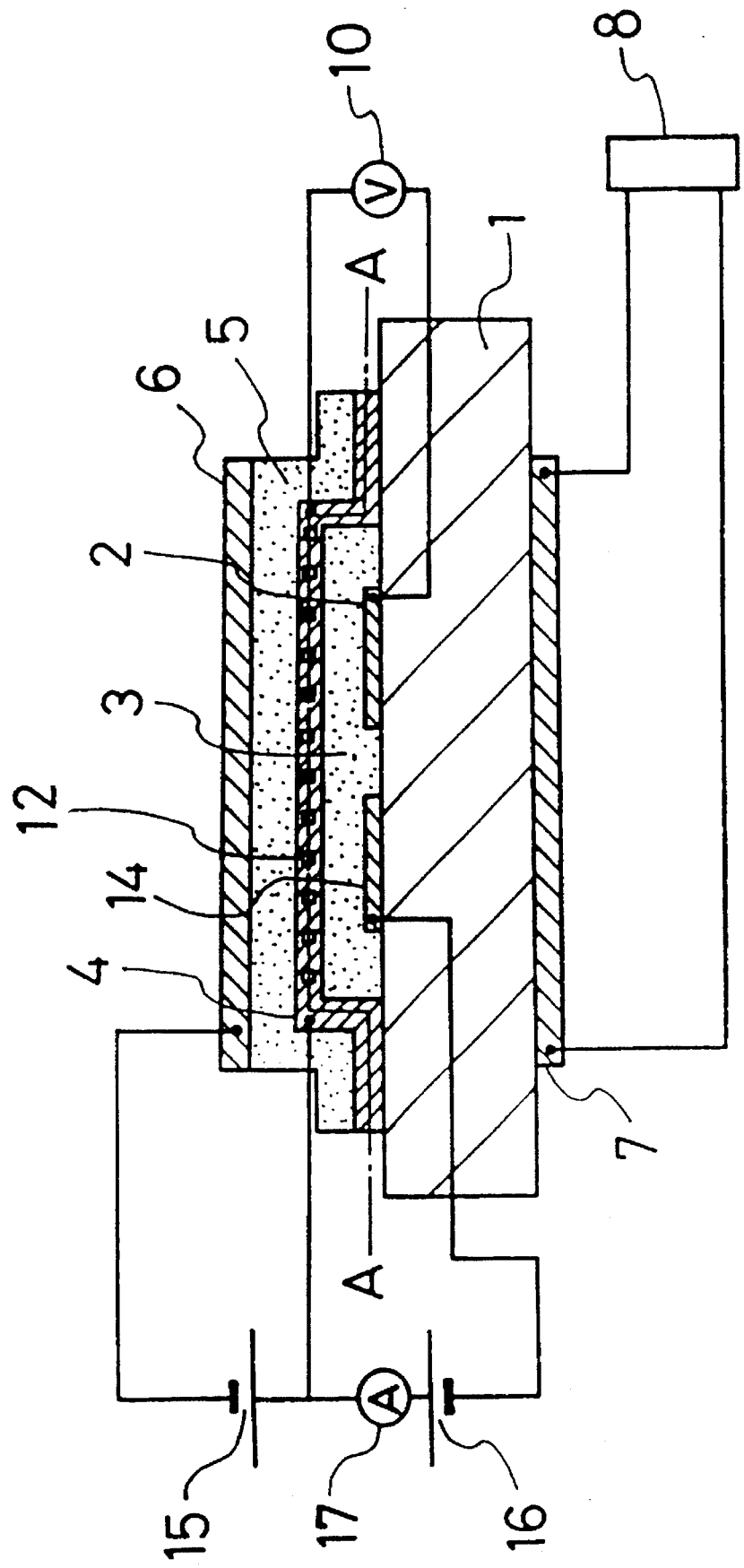
FIG. 14 is a schematic view illustrating an air-fuel ratio sensor according to EXAMPLE 7 of the present invention.

Oxygen Concentration Cell Type Theoretical Air-fuel Ratio Sensor and Limiting Current Type Multi-range Air-fuel Ratio Sensor According to First Aspect of Invention Referring to FIG. 14, a sensor according to EXAMPLE 7 of the present invention is described below. The present sensor has essentially the same structure as that of the sensor described in EXAMPLE 5, except that fine paths 12 communicating with each other are provided densely on the portion of a third electrode 4 as in the sensor of EXAMPLE 3, and that additional paths 13 for communicating the peripheral portion of the path network with the outside are provided on the third electrode 4 in such a manner that they may be connected via the outer peripheral ends of the third electrode 4.

Because the third electrode 4 is porous and the outer peripheral portion thereof is communicated with the outside of the sensor, when the oxygen gas in excess is supplied to the third electrode 4 and the pressure therein is elevated by functioning the oxygen pump, the oxygen gas in excess is discharged to the outside through the fine paths 12 and paths 13. In this manner, the elevation of pressure inside the second electrode 4 can be suppressed and the measurement can be performed without any obstruction. The oxygen gas inside the first electrode 2 and the second electrode 14 is discharged into the porous substrate 1.

The plan- view of the third electrode 4 viewed along line A—A of the sensor described in EXAMPLE 7 is the same as that shown in FIG. 6. In the present example, the paths 12 are cut into a lattice having a predetermined spacing. The paths 13 are provided along the vertical and transversal directions on the outer periphery of the paths 12 to connect the outer periphery of the paths 12 with the outside.

EXAMPLE 8

Figure 15:
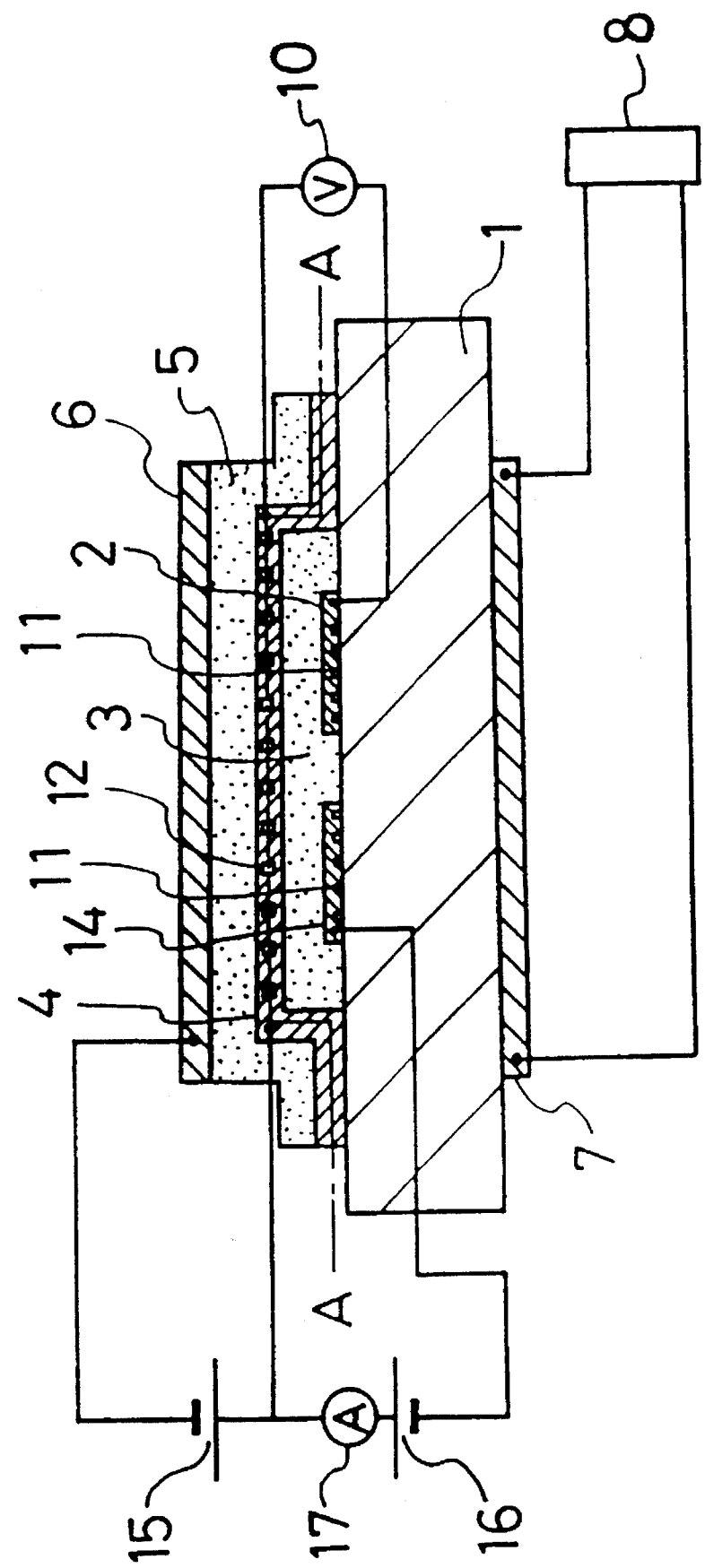
FIG. 15 is a schematic view illustrating an air-fuel ratio sensor according to EXAMPLE 8 of the present invention.

Oxygen Concentration Cell Type Theoretical Air-fuel Ratio Sensor and Limiting Current Type Multi-range Air-fuel Ratio Sensor According to First Aspect of Invention Referring to FIG. 15, a sensor according to EXAMPLE 8 of the present invention is described below. The present sensor has essentially the same structure as that of the sensor described in EXAMPLE 5, except that fine grooves 11 communicating with each other are provided densely on the portion of a first electrode 2 and a second electrode 14 in contact with a porous substrate 1 in a similar manner as in EXAMPLE 6, and that fine paths 12 communicating with each other are provided densely on a third electrode 4, with additional paths 13 for communicating the peripheral portion of the path network with the outside being provided on the third electrode 4, in such a manner that they may be connected via the outer peripheral ends of the third electrode 4, similar to the sensor described to in EXAMPLE 7.

It can be seen therefore that the sensor of the present example possesses both advantages of the sensors described in EXAMPLE 6 and EXAMPLE 7.

The plan view of the first electrode 2 and the second electrode 14 of the sensor according to EXAMPLE 8 is the same as that given in FIG. 4. In the present example, the grooves 11 are cut into a lattice having a predetermined spacing. The plan view of the third electrode 4 of the sensor of EXAMPLE 8 viewed along line A—A is the same as that given in FIG. 6. In the present example, the paths 12 are cut into a lattice having a predetermined spacing. The paths 13 are provided along the vertical and transversal directions on the outer periphery of the paths 12 to connect the outer periphery of the paths 12 with the outside.

EXAMPLE 9

Figure 16:
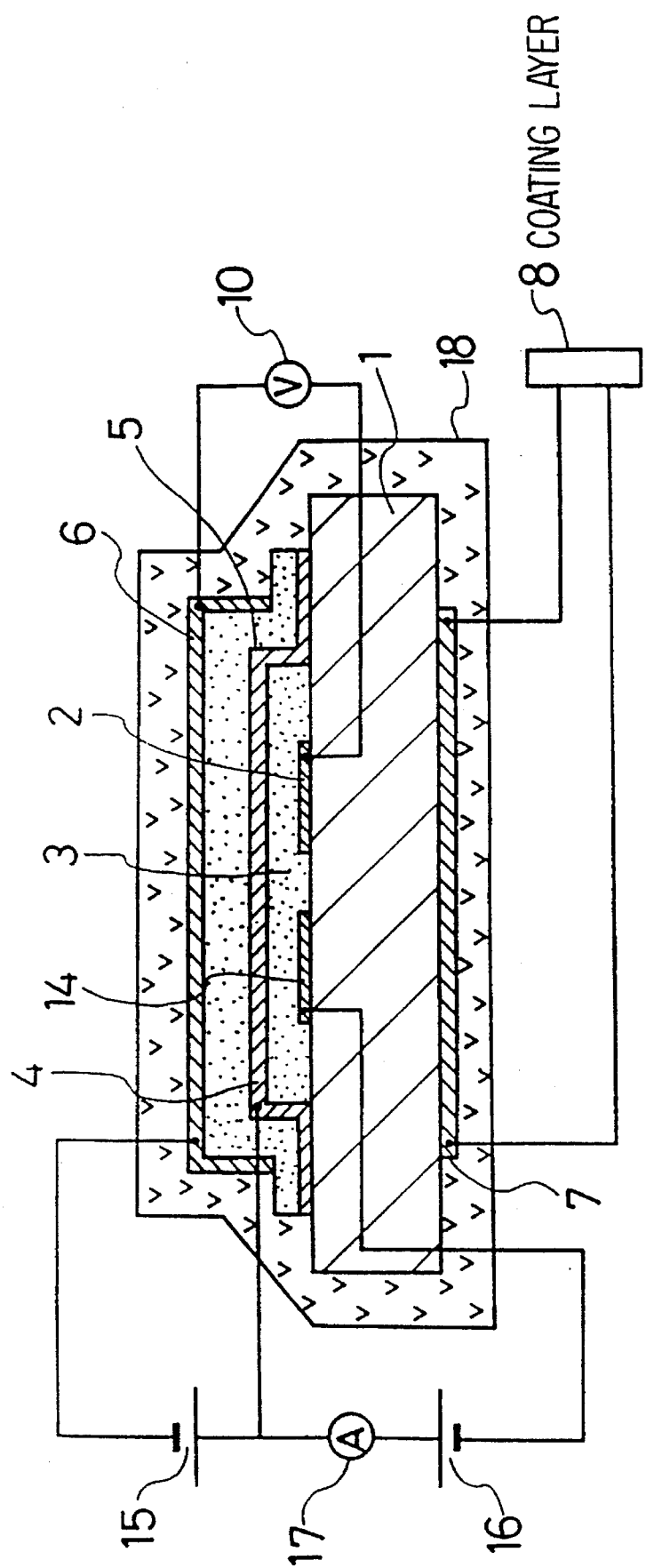
FIG. 16 is a schematic view illustrating an air-fuel ratio sensor according to EXAMPLE 9 of the present invention.

Oxygen Concentration Cell Type Theoretical Air-fuel Ratio Sensor and Limiting Current Type Multi-range Air-fuel Ratio Sensor According to First Aspect of Invention Referring to FIG. 16, a sensor according to EXAMPLE 9 of the present invention is described below. The present sensor has essentially the same structure as that of the sensor described in EXAMPLE 5, except that the entire surface of the sensor element is covered with a coating layer 18 carrying thereon a metal catalyst. The metal catalyst used in the present example is, for example, platinum, and the coating layer may be made of, for instance, alumina. The reason for providing a coating layer 18 carrying thereon a metal catalyst is explained below.

The output current characteristics of a limiting current type multi-range air-fuel ratio sensor and the electromotive characteristics of an oxygen concentration cell type theoretical air-fuel ratio sensor are greatly influenced by the unburnt gas component incorporated in the automobile exhaust gas, i.e., the object to be tested.

In the engine of an automobile, gasoline is mixed with air and then combusted in engine cylinders. The unburnt gas component of each of the gas generated from the cylinders differ from each other in concentration. More specifically, consider a case in which the gas after combustion discharged from the first cylinder is rich in $H_2$, whereas the other gases discharged from the other cylinders are rich in hydrocarbon components. If the sensor were to be installed at a location greatly influenced by the gas discharged from the first cylinder, i.e., a gas rich in unburnt $H_2$, the limiting current type multi-stage air-fuel ratio sensor would yield a high output current, and the oxygen concentration cell type theoretical air-fuel ratio sensor would have its abrupt inflection point in electromotive force curve being shifted to the lean side. If the sensor were to be installed at a location more influenced by the gas discharged from the other cylinders, on the other hand, it can be easily anticipated that the limiting current type multi-stage air-fuel ratio sensor would yield a low output current, and the oxygen concentration cell type theoretical air-fuel ratio sensor would have its abrupt inflection point in electromotive force curve being shifted to the rich side.

As described in the foregoing, the sensor characteristics is subject to the unburnt gas component brought into contact with the sensor. Accordingly, the influence of the unburnt gas components must be minimized. An effective measure for minimizing the influence of the unburnt gas component is to cover the entire sensor element with a coating layer carrying thereon a metal catalyst such as platinum, rhodium, and palladium. The unburnt gas component is completely combusted in the coating layer because of the catalyst incorporated in the coating layer functions on the unburnt component brought into contact with the coating layer. Thus, a gas free of such unburnt components can be provided as the object gas to be tested by the sensor. It can be seen therefore that this measure is effective to obtain a stable sensor output.

The coating layer 18 comprising the metal catalyst may be applied by properly selecting the material, porosity, and thickness of the coating, as well as the type of catalyst to be incorporated therein, the amount of the catalyst, and the like to obtain the desired performance.

EXAMPLE 10

Figure 17:
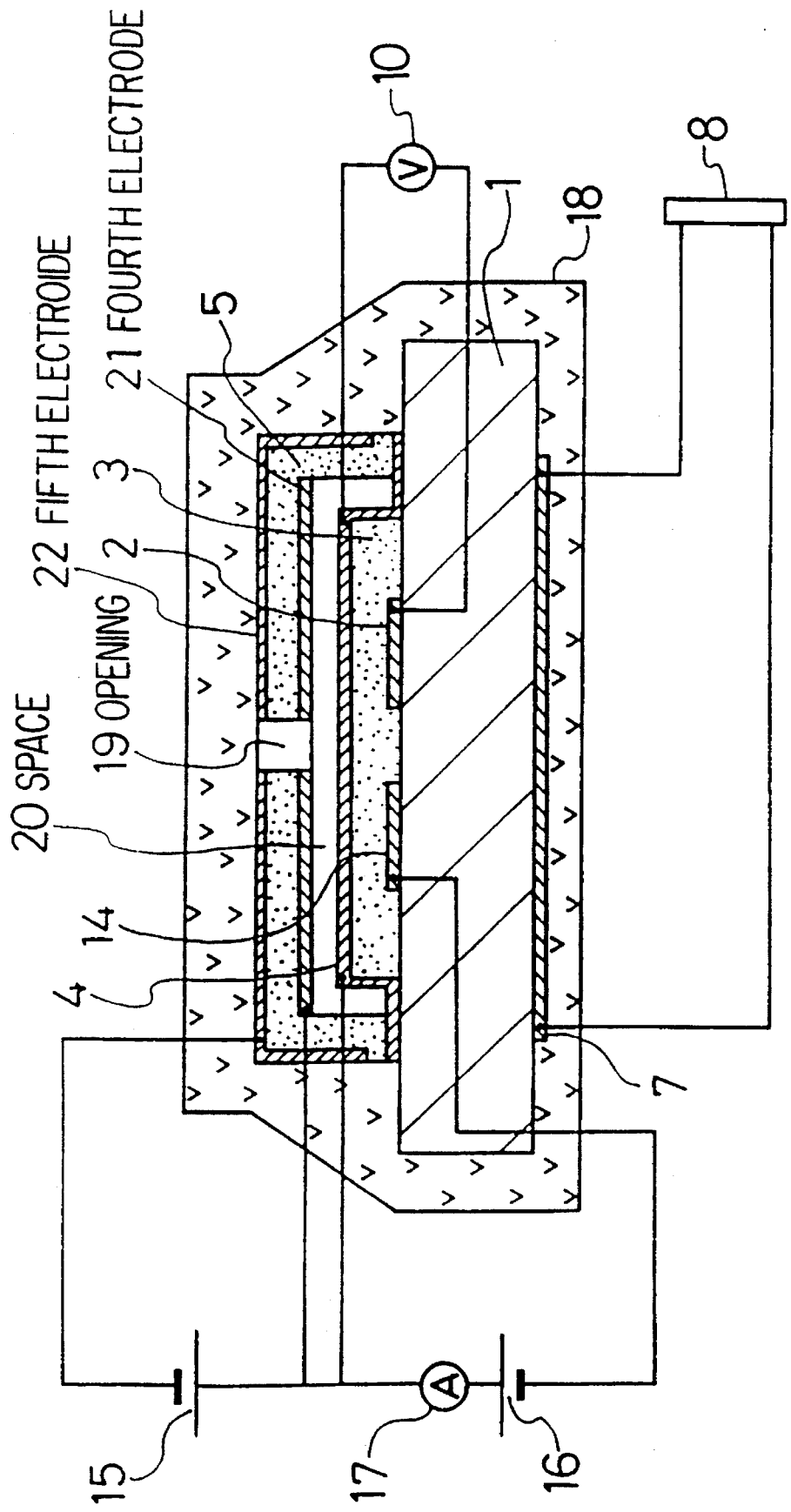
FIG. 17 is a schematic view illustrating an air-fuel ratio sensor according to EXAMPLE 10 of the present invention.

Oxygen Concentration Cell Type Theoretical Air-fuel Ratio Sensor According to Second Aspect of Invention Referring to FIG. 17, a sensor according to EXAMPLE 10 of the present invention is described below. The present sensor according to the second aspect of the present invention differs from the thin film multilayered air-fuel ratio sensor of the first aspect in that a space is provided inside the sensor element. More specifically, the sensor according to the present example comprises a third electrode 4 formed thereon, a second solid electrolyte 5 having an opening 19 (pinhole), the second solid electrolyte 5 being formed in such a manner that a space 20 is provided between the first and second electrolytes 3 and 5, a fourth electrode 21 being formed on the side of the second solid electrolyte 5 on which the third electrode 4 is provided, and a fifth electrode 22 being formed on the second solid electrolyte 4 on the side opposite to that on which the third electrode 4 is formed. The rest of the structure is essentially the same as that of the sensor described in EXAMPLE 9. The function of the space 20 is described below.

In a sensor according to the present example, the excess oxygen is discharged out of the sensor element through the opening 19 when the pressure inside the space 20 is elevated upon functioning the oxygen pump cell. In this manner the oxygen gas pressure inside the space 20 is lowered to maintain a constant oxygen atmosphere at the vicinity of the third electrode 4. This signifies that the third electrode 4 functions as a standard oxygen electrode.

EXAMPLE 11

Figure 18:
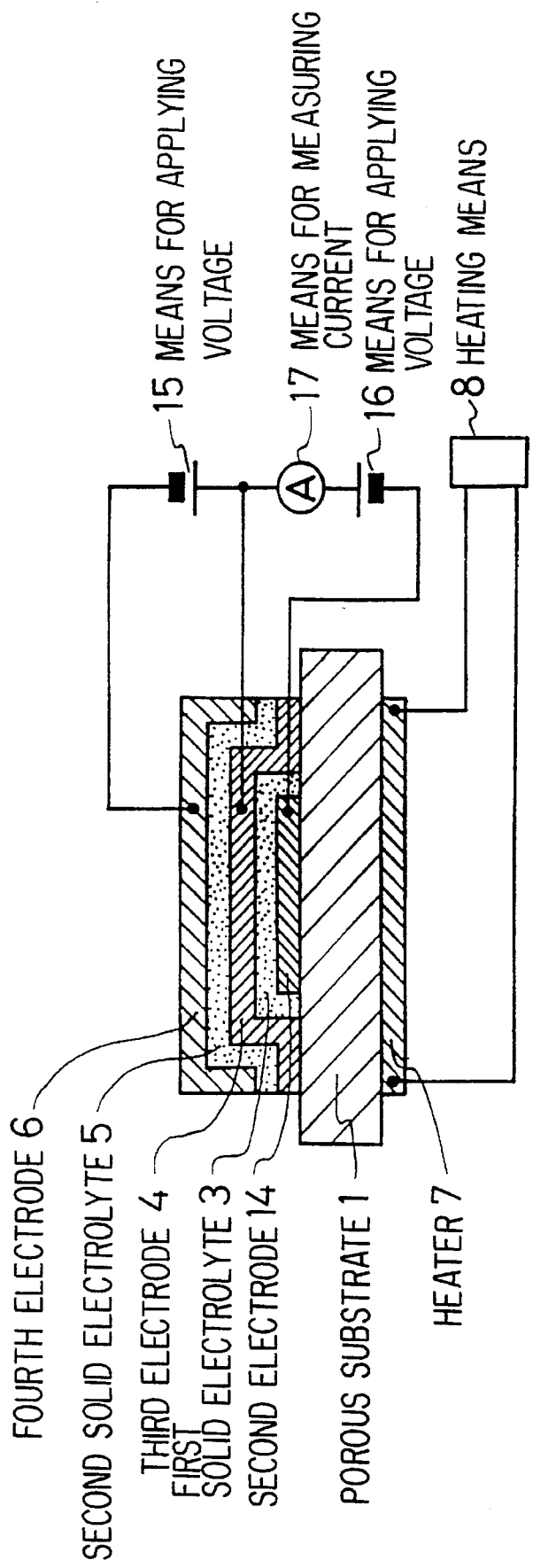
FIG. 18 is a schematic view illustrating an air-fuel ratio sensor according to EXAMPLE 11 of the present invention.

Limiting Current Type Multi-range Air-fuel Ratio Sensor According to First Aspect of Invention Referring to FIG. 18, a sensor according to EXAMPLE 11 is described below. The sensor according to the present example is essentially the same as that described in EXAMPLE 1, except that a second electrode 14 is provided on a porous substrate 1 instead of the first electrode 2 and a limiting current type multi-range air-fuel ratio sensor is provided in the place of the oxygen concentration cell type theoretical air-fuel ratio sensor.

EXAMPLE 12

Figure 19:
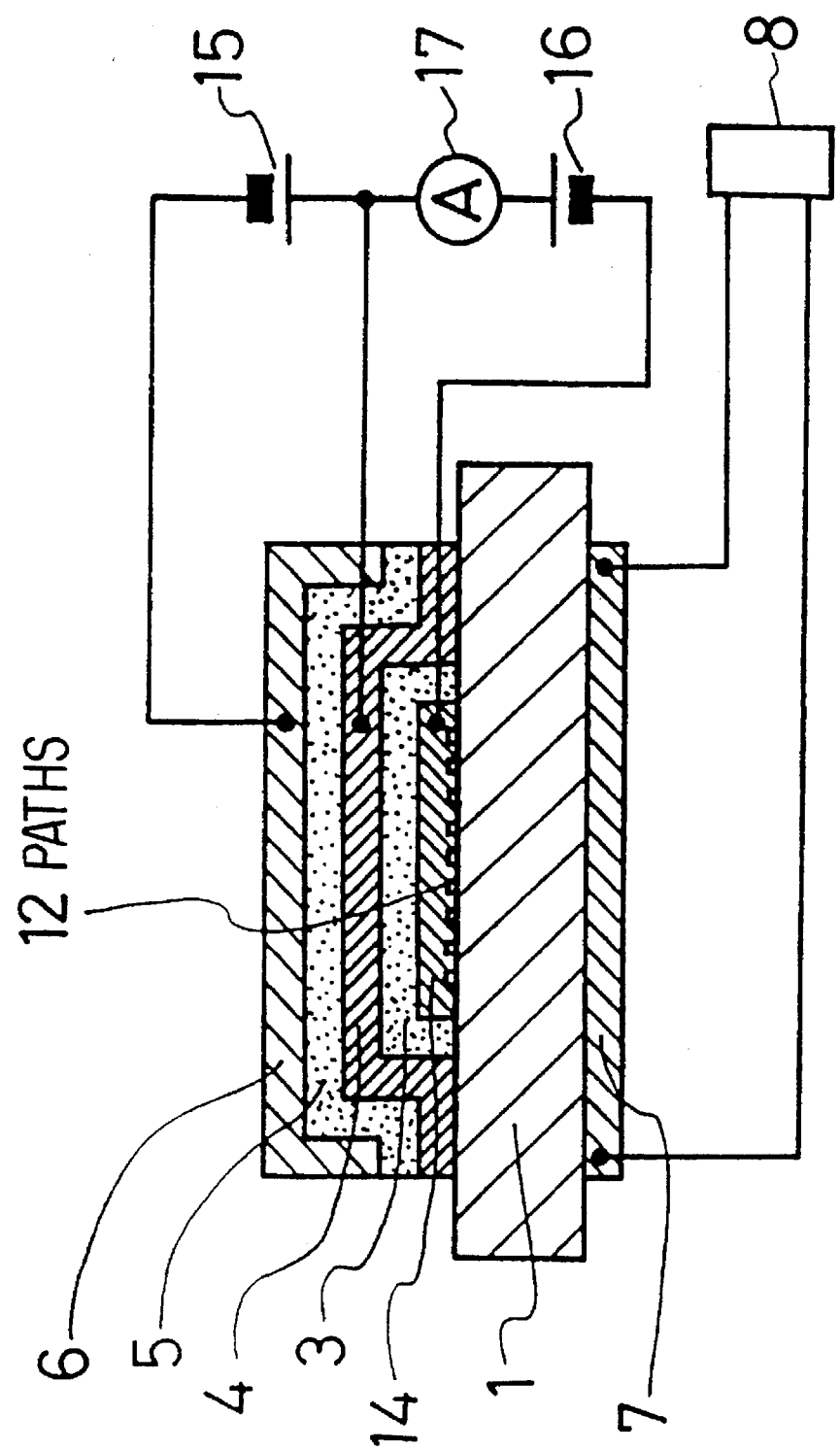
FIG. 19 is a schematic view illustrating an air-fuel ratio sensor according to EXAMPLE 12 of the present invention.

Limiting Current Type Multi-range Air-fuel Ratio Sensor According to First Aspect of Invention Referring to FIG. 19, a sensor according to EXAMPLE 12 is described below. The sensor according to the present example is essentially the same as that described in EXAMPLE 2, except that a limiting current type multi-range air-fuel ratio sensor is provided on a porous substrate 1 in the place of the oxygen concentration cell type theoretical air-fuel ratio sensor.

EXAMPLE 13

Figure 20:
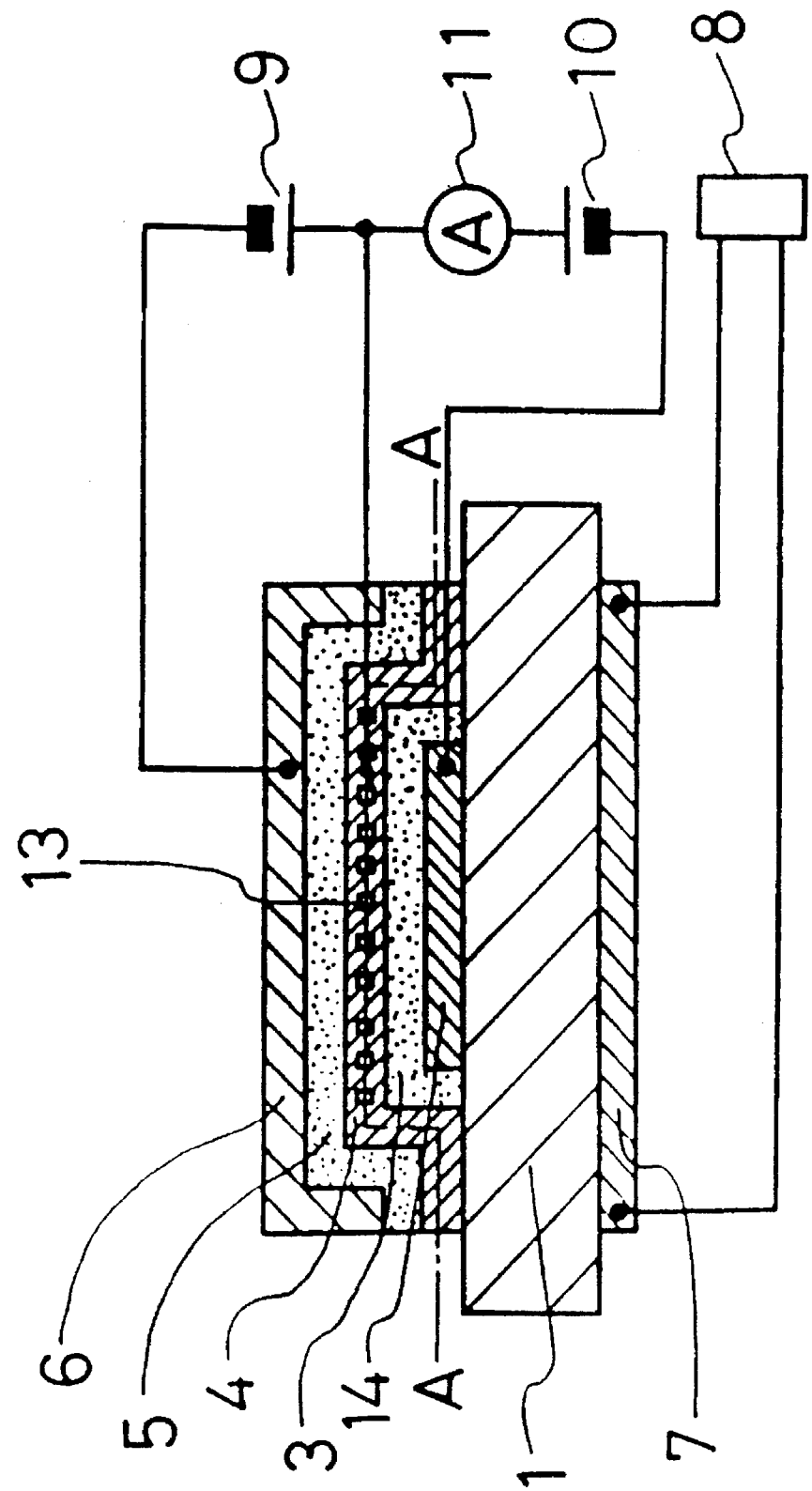
FIG. 20 is a schematic view illustrating an air-fuel ratio sensor according to EXAMPLE 13 of the present invention.

Limiting Current Type Multi-range Air-fuel Ratio Sensor According to First Aspect of Invention Referring to FIG. 20, a sensor according to EXAMPLE 13 is described below. The sensor according to the present example is essentially the same as that described in EXAMPLE 3, except that a limiting current type multi-range air-fuel ratio sensor is provided on a porous substrate 1 in the place of the oxygen concentration cell type theoretical air-fuel ratio sensor.

EXAMPLE 14

Figure 21:
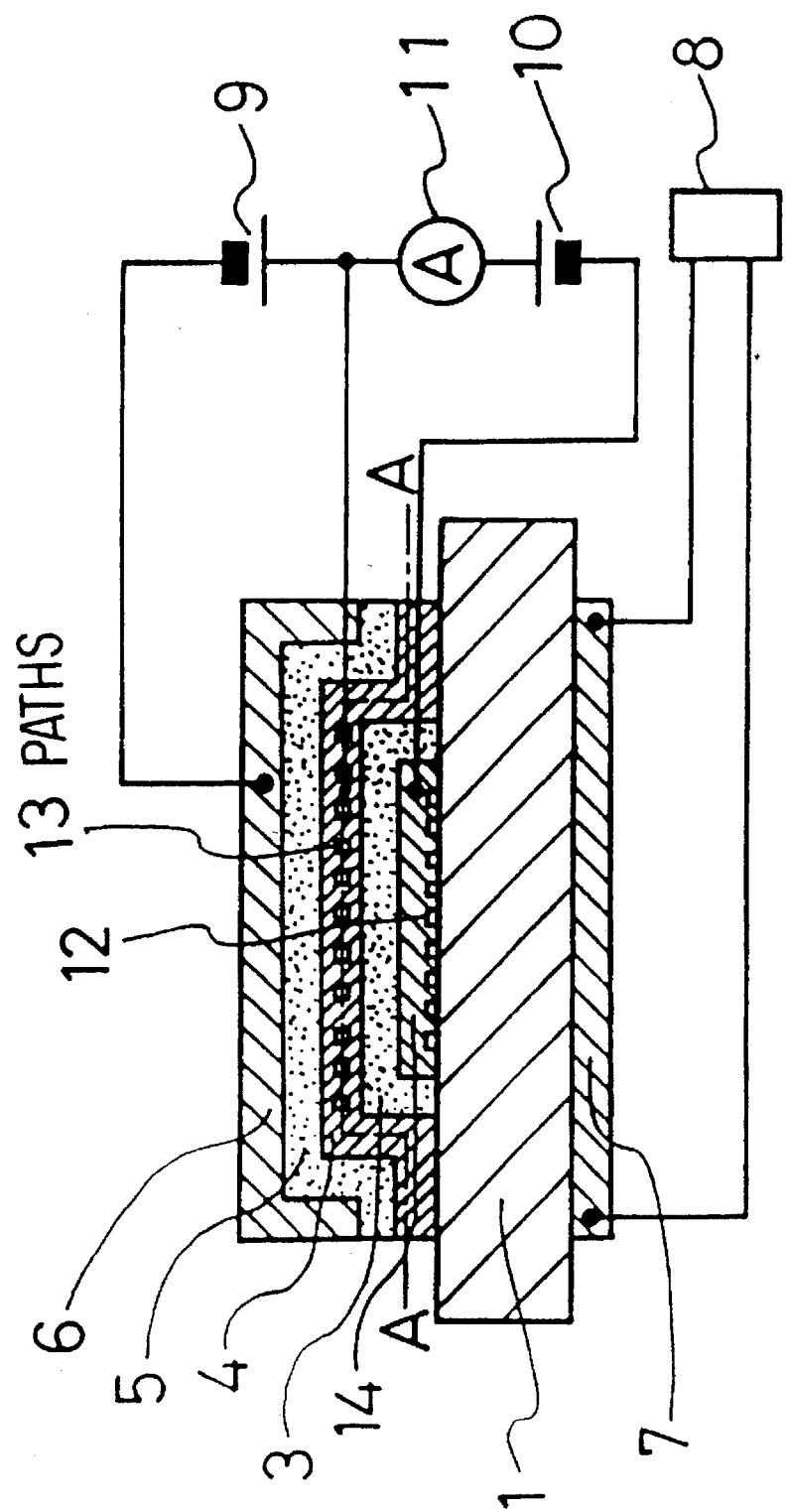
FIG. 21 is a schematic view illustrating an air-fuel ratio sensor according to EXAMPLE 14 of the present invention.

Limiting Current Type Multi-range Air-fuel Ratio Sensor According to First Aspect of Invention Referring to FIG. 21, a sensor according to EXAMPLE 14 is described below. The sensor according to the present example is essentially the same as that described in EXAMPLE 4, except that a limiting current type multi-range air-fuel ratio sensor is provided on a porous substrate 1 in the place of the oxygen concentration cell type theoretical air-fuel ratio sensor.

As described in the foregoing, the sensor according to the present invention comprises an oxygen pump cell which functions as a reference electrode corresponding to a prior art atmospheric reference electrode, and an oxygen concentration cell type theoretical air-fuel ratio sensor and/or a limiting current type multi-range air-fuel ratio sensor being integrated into a single sensor. Accordingly, the theoretical air-fuel ratio can be detected with high precision from the abruptly changing characteristics of the electromotive force measured on the oxygen concentration cell type theoretical air-fuel ratio sensor. Furthermore, an air-fuel ratio ranging over a wide range from a rich region to lean region can be detected from the output current obtained on the limiting current type multi-range air-fuel ratio sensor.

While the invention has been described in detail and with reference to specific embodiments thereof, it will be apparent to one skilled in the art that various changes and modifications can be made therein without departing from the spirit and scope thereof.

What is claimed is:

1. A thin film multilayered air-fuel ratio sensor having a sensor element comprising:

a first electrode formed on a porous substrate;

a first solid electrolyte and a second electrode formed on the first electrode in this order, in such a manner that the first electrode is completely covered by the first solid electrolyte and that the first solid electrolyte is completely covered by the second electrode and a second solid electrolyte and a third electrode formed on the second electrode in this order, in such a manner that the peripheral portion of the second electrode is left uncovered by the second solid electrolyte and the third electrode and thereby left exposed;

the first electrode, the second electrode and the third electrode being made of a gas-permeable porous platinum, and the first solid electrolyte and the second solid electrolyte being made of a gas-impermeable dense solid electrolyte having oxygen ion conductivity.

2. A thin film multilayered air-fuel ratio sensor as claimed in claim 1, wherein a plurality of fine grooves communicating with each other are densely provided on the portion of the first electrode in contact with the porous substrate.

3. A thin film multilayered air-fuel ratio sensor as claimed in claim 1, wherein a plurality of fine paths communicating with each other are densely provided on the second electrode; and a path connecting an outer peripheral portion of the plurality of said paths with the outside is further provided on the second electrode at an outer peripheral portion of said second electrode.

4. A thin film multilayered air-fuel ratio sensor as claimed in claim 1, wherein a plurality of fine grooves communicating with each other are densely provided on a portion of the first electrode in contact with the porous substrate;

a plurality of fine paths communicating with each other are densely provided on the second electrode; and a path communicating with an outer peripheral portion of the plurality of said paths with the outside is further provided on the second electrode at an outer peripheral portion of said second electrode.

5. A thin film multilayered air-fuel ratio sensor as claimed in claim 1, having the sensor element comprising the porous substrate and the following portions formed integratedly thereon:

a portion which functions as an oxygen concentration cell theoretical air-fuel ratio sensor, comprising the first electrode, the first solid electrolyte, and the second electrode; and a portion which functions as an oxygen pump cell, comprising the second electrode, the second solid electrolyte and the third electrode.

6. A thin film multilayered air-fuel ratio sensor as claimed in claim 1, further comprising a fourth electrode formed on the porous substrate in addition to the first electrode and having the sensor element comprising the porous substrate and the following portions formed integratedly thereon:

a portion which functions as a limiting current multi-range air-fuel ratio sensor, comprising the fourth electrode, the first solid electrolyte, and the second electrode; and a portion which functions as an oxygen pump cell, comprising the second electrode, the second solid electrolyte, and the third electrode.

7. A thin film multilayered air-fuel ratio sensor having a sensor element comprising a porous substrate and the following portions formed integratedly thereon:

a first electrode formed on a porous substrate;

a first solid electrolyte and a second electrode formed on the first electrode in this order, in such a manner that the first electrode is completely covered by the first solid electrolyte, and that the first solid electrolyte is completely covered by the second electrode; and a second solid electrolyte and a third electrode formed on the second electrode in this order, in such a manner that the peripheral portion of the second electrode is left uncovered by the second solid electrolyte and the third electrode and thereby left exposed;

the first electrode, the second electrode and the third electrode being made of a gas-permeable porous platinum, and the first solid electrolyte and the second solid electrolyte being made of a gas-impermeable dense solid electrolyte having oxygen ion conductivity, a portion which functions as a limiting current multi-range air-fuel ratio sensor, comprising the first electrode, the first solid electrolyte, and the second electrode; and a portion which functions as an oxygen pump cell, comprising the second electrode, the second solid electrolyte, and the third electrode.

8. A thin film multilayered air-fuel ratio sensor having a sensor element comprising:

a first electrode formed on a porous substrate;

a first solid electrolyte and a second electrode formed on the first electrode in this order, in such a manner that the first electrode is completely covered by the first solid electrolyte, and that the first solid electrolyte is completely covered by the second electrode;

a second solid electrolyte having an opening formed in such a manner that a space is provided between the first solid electrolyte and the second solid electrolyte; and a third electrode formed on the side of the second solid electrolyte facing the second electrode and a fourth electrode formed on the side of the second solid electrolyte opposite to that facing the second electrode, the second solid electrolyte and the fourth electrode being formed in such a manner that the peripheral portion of the second electrode is left uncovered by the second electrolyte and the fourth electrode and therefore left exposed;

the first electrode, the second electrode, the third electrode and the fourth electrode being made of a gas-permeable porous platinum, and the first solid electrolyte and the second solid electrolyte being made of a gas-impermeable dense solid electrolyte having oxygen ion conductivity.

9. A thin film multilayered air-fuel ratio sensor as claimed in claim 8, having the sensor element comprising the porous substrate and the following portions formed integratedly thereon:

a portion which functions as an oxygen concentration cell theoretical air-fuel ratio sensor, comprising the first electrode, the first solid electrolyte, and the second electrode; and a portion which functions as an oxygen pump cell, comprising the fourth electrode, the second solid electrolyte, and the third electrode.

10. A thin film multilayered air-fuel ratio sensor as claimed in claim 8, further comprising a fifth electrode formed on the porous substrate in addition to the first electrode and having the sensor element comprising the porous substrate and the following portions formed integratedly thereon:

a portion which functions as a limiting current multi-range air-fuel ratio sensor, comprising the fifth electrode, the first solid electrolyte and the second electrode; and a portion which functions as an oxygen pump cell, comprising the fourth electrode, the second solid electrolyte, and the third electrode.

11. A thin film multilayered air-fuel ratio sensor having a sensor element comprising:

a first electrode formed on a porous substrate;

a first solid electrolyte and a second electrode formed on the first electrode in this order, in such a manner that the first electrode is completely covered by the first solid electrolyte, and that the first solid electrolyte is completely covered by the second electrode;

a second solid electrolyte having an opening formed in such a manner that a space is provided between the first solid electrolyte and the second solid electrolyte;

a third electrode formed on the side of the second solid electrolyte facing the second electrode and a fourth electrode formed on the side of the second solid electrolyte opposite to that facing the second electrode, the second solid electrolyte and the fourth electrode being formed in such a manner that the peripheral portion of the second electrode is left uncovered by the second electrolyte and the fourth electrode and thereby left exposed;

the first electrode, the second electrode, the third electrode and the fourth electrode being made of a gas-permeable porous platinum, and the first solid electrolyte and the second solid electrolyte being made of a gas-impermeable dense solid electrolyte having oxygen ion conductivity;

a portion which function as a limiting current multi-range air-fuel ratio sensor, comprising a fifth electrode on the porous substrate, the first solid electrolyte, and the second electrode; and a portion which functions as an oxygen pump cell, comprising the third electrode, the second solid electrolyte and the fourth electrode.

* * * * *